United States Patent
Kanai

(10) Patent No.: US 7,338,439 B2
(45) Date of Patent: Mar. 4, 2008

(54) CONDENSING OPTICAL SYSTEM, CONFOCAL OPTICAL SYSTEM, AND SCANNING CONFOCAL ENDOSCOPE

(75) Inventor: Moriyasu Kanai, Saitama-ken (JP)

(73) Assignees: PENTAX Corporation, Tokyo (JP); Optiscan Pty Ltd., Victoria (AU)

( * ) Notice: Subject to any disclaimer, the term of this patent is extended or adjusted under 35 U.S.C. 154(b) by 707 days.

(21) Appl. No.: 10/933,308

(22) Filed: Sep. 3, 2004

(65) Prior Publication Data

US 2005/0052753 A1  Mar. 10, 2005

(30) Foreign Application Priority Data

Sep. 5, 2003 (JP) ............................. 2003-314204
Oct. 17, 2003 (JP) ............................. 2003-357896

(51) Int. Cl.
*A61B 1/00* (2006.01)
*G02B 26/10* (2006.01)

(52) U.S. Cl. ................. 600/176; 600/113; 359/205

(58) Field of Classification Search .............. 600/182, 600/176, 113; 359/205, 389
See application file for complete search history.

(56) References Cited

U.S. PATENT DOCUMENTS

| | | | |
|---|---|---|---|
| 5,161,053 A | 11/1992 | Dabbs | |
| 5,742,419 A | 4/1998 | Dickensheets et al. | |
| 5,836,869 A | 11/1998 | Kudo et al. | |
| 5,907,425 A | 5/1999 | Dickensheets et al. | |
| 6,409,666 B1 | 6/2002 | Ito | |
| 6,483,626 B2 | 11/2002 | Suga | |
| 6,545,260 B1* | 4/2003 | Katashiro et al. | ...... 250/227.26 |
| 7,267,647 B2* | 9/2007 | Okada et al. | ............... 600/166 |
| 2003/0072067 A1* | 4/2003 | Hashimura | ................... 359/205 |
| 2003/0178558 A1* | 9/2003 | Fukuyama | ................... 250/234 |
| 2005/0167508 A1* | 8/2005 | Syms et al. | ................. 235/473 |
| 2006/0056017 A1* | 3/2006 | Berier et al. | ............... 359/380 |
| 2006/0170930 A1* | 8/2006 | Li | .............................. 356/479 |

FOREIGN PATENT DOCUMENTS

| | | |
|---|---|---|
| JP | 8-332169 | 12/1996 |
| JP | 9-230248 | 9/1997 |
| JP | 2000-258699 | 9/2000 |
| JP | 2000-292703 | 10/2000 |

OTHER PUBLICATIONS

English Language Abstract of JP 2000-292703. Oct. 2000.
U.S. Appl. No. 10/774,540, no date.

* cited by examiner

*Primary Examiner*—John P. Leubecker
(74) *Attorney, Agent, or Firm*—Greenblum & Bernstein, P.L.C.

(57) ABSTRACT

A condensing optical system, suitable for a scanning confocal optical system (having a composition for scanning a beam spot on a subject surface by swinging a point source of light) and capable of satisfactorily suppressing various aberrations and reducing loss of light quantity, is provided. The condensing optical system, installed in a scanning confocal optical system for obtaining images of a subject surface by scanning a beam emitted from a point source of light by moving the point source which serves as a pinhole for confocal observation, is configured to satisfy the following condition $$0.1 < |m \times NA| < 0.2$$

where "m" denotes magnification of the condensing optical system and "NA" denotes a numerical aperture of the condensing optical system on its subject surface side.

28 Claims, 17 Drawing Sheets

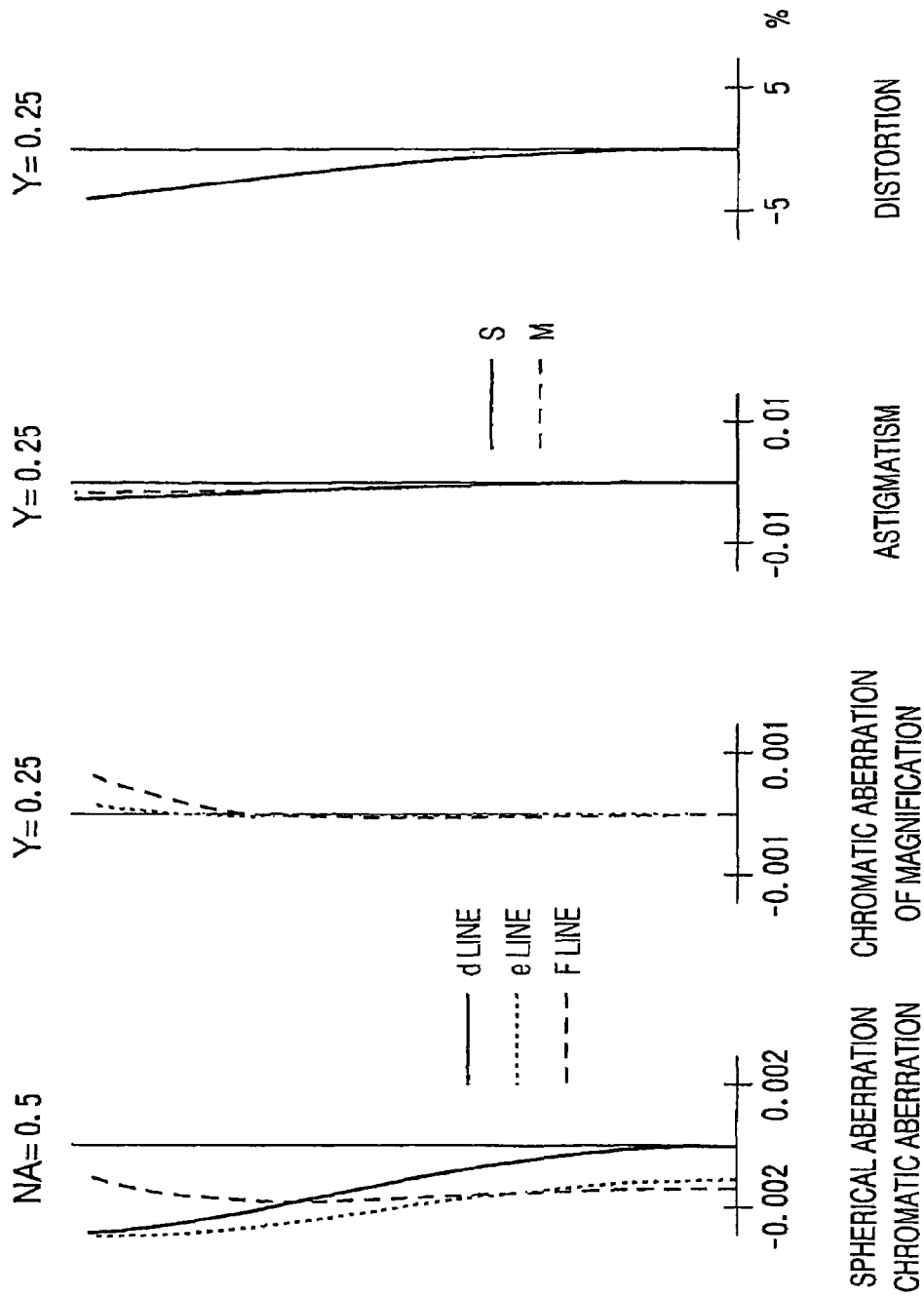

CONDENSING OPTICAL SYSTEM, CONFOCAL OPTICAL SYSTEM, AND SCANNING CONFOCAL ENDOSCOPE

BACKGROUND OF THE INVENTION

The present invention relates to a confocal optical system installed in a scanning confocal endoscope which enables observation of tomograms of a tissue in a body cavity.

Confocal probes employing an optical system of a confocal microscope (capable of obtaining images of higher magnification and resolution than ordinary endoscope optical systems) as their probes and scanning confocal endoscopes employing such a confocal probe are well known. The confocal probe applies a laser beam as illuminating light to a living tissue (subject) in a body cavity and selectively receives reflected light or fluorescence from the tissue that is on the object-side focal plane of its objective optical system. In other words, the confocal probe extracts light that is on the focal plane from the reflected light or fluorescence from the tissue. Probes are generally classified into direct view probes (applying the illuminating light to the tissue from their tips) and lateral view probes (applying the illuminating light to the tissue from their lateral faces). The type of optical path required varies depending on whether the probe is a direct view probe or a lateral view probe, therefore, the optical system for each probe has to be designed properly depending on the type of the probe.

Optical systems usable for a confocal probe have been disclosed in Japanese Patent Provisional Publication No. 2000-292703 (hereinafter referred to as "patent document #1") and Japanese Patent Provisional Publication No. 2000-258699 (hereinafter referred to as "patent document #2"), for example. The patent document #1 discloses an optical system usable for a lateral view confocal probe.

The optical system of the patent document #1 scans or dynamically deflects a beam on a living tissue (subject surface) by use of reflecting surfaces of mirrors, for example. Therefore, the distance between the light source and the objective lens (condensing optical system) is set long enough for securing a space for placing the reflecting surface and thereby the diameter of the objective lens is necessitated to be large and attaining a sufficiently wide scan range becomes difficult. Moreover, the space where the reflecting surface is placed is required to further include a space for driving the reflecting surface in a prescribed direction.

Further, in the patent document #1, the aperture stop and the first surface of the condensing optical system are provided with reflecting surfaces and the scanning of the beam is realized while securing a necessary optical path length by letting the beam travel to and fro between the aperture stop and the first surface. Therefore, loss of light quantity occurs on each reflection of the beam and it is impossible to use the beam efficiently. Moreover, the optical system of the patent document #1 does not have a mechanism for changing the condensing position (focal position) of the beam in the depth direction of the subject, that is, in the optical axis direction of the objective lens. Thus, it is impossible to detect the position of the subject surface accurately and obtain high definition images of the subject.

By the way, in recent years, a scanning confocal endoscope of an integrated type having functions of a conventional endoscope and a confocal probe (hereinafter simply referred to as an "integrated endoscope") is being hoped for in order to reduce the load on operators for handling probes. Such an integrated endoscope is required to include both a first optical system for general endoscope observation (hereinafter called "general observation") and a second optical system for the so-called "confocal observation", independently. Therefore, reducing the diameter of the flexible tube (endoscope) by miniaturizing each optical system (especially, the optical system for the confocal observation) becomes the most critical challenge. However, application of the composition of the above patent document #1 or #2 to the confocal observation optical system causes increased diameter and length of the flexible tube. Meanwhile, for realizing widest-range scanning of the beam while miniaturizing the flexible tube, it is possible to let the confocal observation optical system adopt an optical system which scans a beam spot on the subject surface by swinging the point source of light (U.S. Pat. No. 5,161,053, for example).

However, there have been no concrete discussions or propositions on a condensing optical system that is suitable for the case where the swinging of the point source of light is employed for the optical system for the confocal observation, that is, a condensing optical system for a confocal observation optical system capable of satisfactorily reducing the loss of light quantity and suppressing various aberrations.

SUMMARY OF THE INVENTION

It is therefore the primary object of the present invention to provide a condensing optical system suitable for a confocal optical system having the aforementioned composition for scanning a beam spot on the subject surface by swinging the point source of light. Specifically, the present invention aims to provide such a condensing optical system capable of satisfactorily suppressing various aberrations and reducing the loss of light quantity.

Another object of the present invention is to provide a confocal optical system including such a condensing optical system suitable for the composition which scans the beam spot on the subject surface by swinging the point source of light, capable of securing a wide scan range while being small-sized.

In accordance with an aspect of the present invention, there is provided a condensing optical system installed in a scanning confocal optical system for obtaining images of a subject surface by scanning a beam emitted from a point source of light which serves as a pinhole for confocal observation. The condensing optical system is configured to satisfy the following condition (1):

$$0.1 < |m \times NA| < 0.2 \qquad (1)$$

where "m" denotes magnification of the condensing optical system and "NA" denotes a numerical aperture of the condensing optical system on its subject surface side.

Incidentally, the point source of light is moved typically on a surface substantially parallel to the end face of the flexible tube endoscope, that is, on a surface substantially orthogonal to the optical axis of the condensing optical system.

In a preferred embodiment, the condensing optical system comprises a first group having positive power, a second group including at least a lens with a concave surface facing toward the subject surface, and a third group having positive power, from the point source side of the condensing optical system. The first group condenses a diverging beam emitted from the point source of light by its positive power.

In the condensing optical system composed as above, it is desirable that the following conditions (2) and (3) be satisfied:

$$0.1 < d0/f1 < 0.5 \qquad (2)$$

$$0.2 < |f1/f| < 2.0 \qquad (3)$$

where "d0" denotes a distance from the point source of light to a first surface of the condensing optical system, "f" denotes a composite focal length of the whole condensing optical system, and "f1" denotes a focal length of the first group.

Preferably, the third group may include the following three groups from its point source side: a group 3A including at least one positive single lens and a cemented lens made of a positive lens and a negative lens, having positive power as a whole; a group 3B including a cemented lens made of a biconcave lens and a biconvex lens, having negative power as a whole; and a group 3C including at least one positive single lens, having positive power as a whole.

Preferably, the first group may be composed of a single lens having an Abbe number v1 satisfying the following condition (4):

$$v1 < 30 \qquad (4)$$

Preferably, the group 3A includes two single lenses having positive power. Meanwhile, the group 3C may preferably include a biconvex lens and a positive meniscus lens. By such distribution of positive power to two or more lenses in each group, spherical aberration and coma can be suppressed well even when a spherical lens is used for each group.

Preferably, the second group includes a single lens or a cemented lens. The single lens or cemented lens may be configured to have a concave surface functioning as a field flattener.

In another preferred embodiment, the condensing optical system comprises a first group having positive power, a deflecting group including at least one deflecting member, a second group having positive power, and a cover glass, from its point source side. The condensing position of the beam condensed by the condensing optical system is moved in an optical axis direction of the condensing optical system at least by changing a distance between the second group and the cover glass.

By such composition, the beam from the point source of light can be emitted from a lateral face of the flexible tube.

Preferably, the first group may include the following three groups from its point source side: a group 1A having positive power, a group 1B including either a single lens or cemented lens with at least a concave surface facing toward the cover glass, and a group 1C having positive power including a cemented lens and a single lens.

In the condensing optical system composed as above, it is desirable that the following conditions (2a) and (3a) be satisfied:

$$0.1 < d0/f1A < 0.5 \qquad (2a)$$

$$0.2 < |f1A/f1| < 0.8 \qquad (3a)$$

where "d0" denotes a distance from the point source of light to a first surface of the condensing optical system, "f1" denotes a composite focal length of the first group, and "f1A" denotes a focal length of the group 1A.

Preferably, the group 1A may be composed of a single lens having an Abbe number v1A satisfying the following condition (4a):

$$v1A < 30 \qquad (4a)$$

In order to reduce the number of lenses and simplify the condensing optical system, the group 1A may be implemented by a single lens.

It is desirable that the second group should include at least one positive single lens and a cemented lens made of a positive lens and a negative lens.

Preferably, the second group includes three positive single lenses.

Preferably, the condensing optical system is configured so that the beam emerging from the deflecting group and incident upon the second group will be substantially a parallel beam.

In such an optical system having an optical path that is deflected in the middle of the system, maintaining high accuracy of assembly of the groups before and after the deflecting group is extremely difficult. In order to reduce the assembly error and suppress aberrations caused by the decentering, not only the beam incident upon the second group but also the beam emerging from the first group should be a substantially parallel beam. Therefore, it is preferable that the first group and the second group satisfy the following condition (5a):

$$0.97 < f2 \times m/f1 < 1.03 \qquad (5a)$$

where "f1" denotes a composite focal length of the first group, "f2" denotes a composite focal length of the second group, and "m" denotes magnification of the condensing optical system. In the optical system satisfying the condition (5a), it is desirable that the deflecting group be formed of optical members that are made of planes only, in order to let the parallel beam from the first group enter the second group intact as a parallel beam.

The deflecting group may preferably be implemented by one or more prisms so that the in-air length will be shorter than that of a deflecting group made of mirrors. The deflection of the beam is realized by letting at least one optical surface of the prism totally reflect the incident beam, by which loss of light quantity during the deflection can be minimized.

Preferably, the angle θ between the optical axis of the first group and that of the second group is set to satisfy the following condition (6a):

$$35° < \theta < 105° \qquad (6a)$$

The condition (6) is for letting the deflecting group satisfy the total reflection condition.

More preferably, the first group, the deflecting group and the cover glass are fixed inside the scanning confocal optical system.

In accordance with another aspect of the present invention, there is provided a confocal optical system comprising: a point source of light serving as a pinhole for confocal observation; a condensing optical system for condensing a beam emitted from the point source; a cover glass provided between the condensing optical system and a condensing position of the beam condensed by the condensing optical system; a scanning unit for scanning the beam by moving the point source of light at least on a surface substantially orthogonal to an optical axis of the condensing optical system; and a condensing position moving unit for moving the condensing position in an optical axis direction of the condensing optical system by changing a distance between the condensing optical system and the cover glass. In the confocal optical system, the condensing optical system is configured to satisfy the following condition (1)

$$0.1 < |m \times NA| < 0.2 \qquad (1)$$

where "m" denotes magnification of the condensing optical system and "NA" denotes a numerical aperture of the condensing optical system on its subject surface side.

Preferably, the surface substantially orthogonal to the optical axis of the condensing optical system is a curved surface having its center of curvature on the optical axis of the condensing optical system, and the confocal optical system is configured to satisfy the following condition (5):

$$0.1 < -f/s < 1.0 \quad (5)$$

where "f" denotes a composite focal length of the whole condensing optical system and "s" denotes a distance from a front principal point of the condensing optical system to an intersection point of the optical axis of the condensing optical system and an elongation of a principal ray of the beam emitted from the moving point source regarding a direction toward the subject surface as positive.

More specifically, the point source of light is an emitting end of an optical fiber which is provided between a light emitting unit and the condensing optical system to be substantially coaxial with the optical axis of the condensing optical system, and the scanning unit moves the point source of light on the curved surface by bending a part of the optical fiber in the vicinity of the emitting end.

In accordance with another aspect of the present invention, there is provided a confocal optical system comprising: a point source of light serving as a pinhole for confocal observation; a condensing optical system for condensing a beam emitted from the point source, including a first group having positive power, a deflecting group including at least one deflecting member, a second group having positive power, and a cover glass from its point source side; a scanning unit for scanning the beam by moving the point source of light at least on a surface substantially orthogonal to an optical axis of the condensing optical system; and a condensing position moving unit for moving a condensing position of the beam condensed by the condensing optical system in an optical axis direction of the condensing optical system at least by changing a distance between the second group and the cover glass.

In accordance with another aspect of the present invention, there is provided a scanning confocal endoscope, comprising a confocal optical system including: a point source of light serving as a pinhole for confocal observation; a condensing optical system for condensing a beam emitted from the point source, being configured to satisfy the following condition (1):

$$0.1 < |m \times NA| < 0.2 \quad (1)$$

where "m" denotes magnification of the condensing optical system and "NA" denotes a numerical aperture of the condensing optical system on its subject surface side; a cover glass provided between the condensing optical system and a condensing position of the beam condensed by the condensing optical system; a scanning unit for scanning the beam by moving the point source of light at least on a surface substantially orthogonal to an optical axis of the condensing optical system; and a condensing position moving unit for moving the condensing position in an optical axis direction of the condensing optical system by changing a distance between the condensing optical system and the cover glass.

In accordance with another aspect of the present invention, there is provided a scanning confocal endoscope, comprising a confocal optical system including: a point source of light serving as a pinhole for confocal observation; a condensing optical system for condensing a beam emitted from the point source, including a first group having positive power, a deflecting group including at least one deflecting member, a second group having positive power, and a cover glass from its point source side; a scanning unit for scanning the beam by moving the point source of light at least on a surface substantially orthogonal to an optical axis of the condensing optical system; and a condensing position moving unit for moving a condensing position of the beam condensed by the condensing optical system in an optical axis direction of the condensing optical system at least by changing a distance between the second group and the cover glass.

BRIEF DESCRIPTION OF THE DRAWINGS

FIGS. 16A through 16D are graphs showing aberrations occurring in the condensing optical system of the second example of the second embodiment.

DESCRIPTION OF THE PREFERRED EMBODIMENTS

Figure 1:
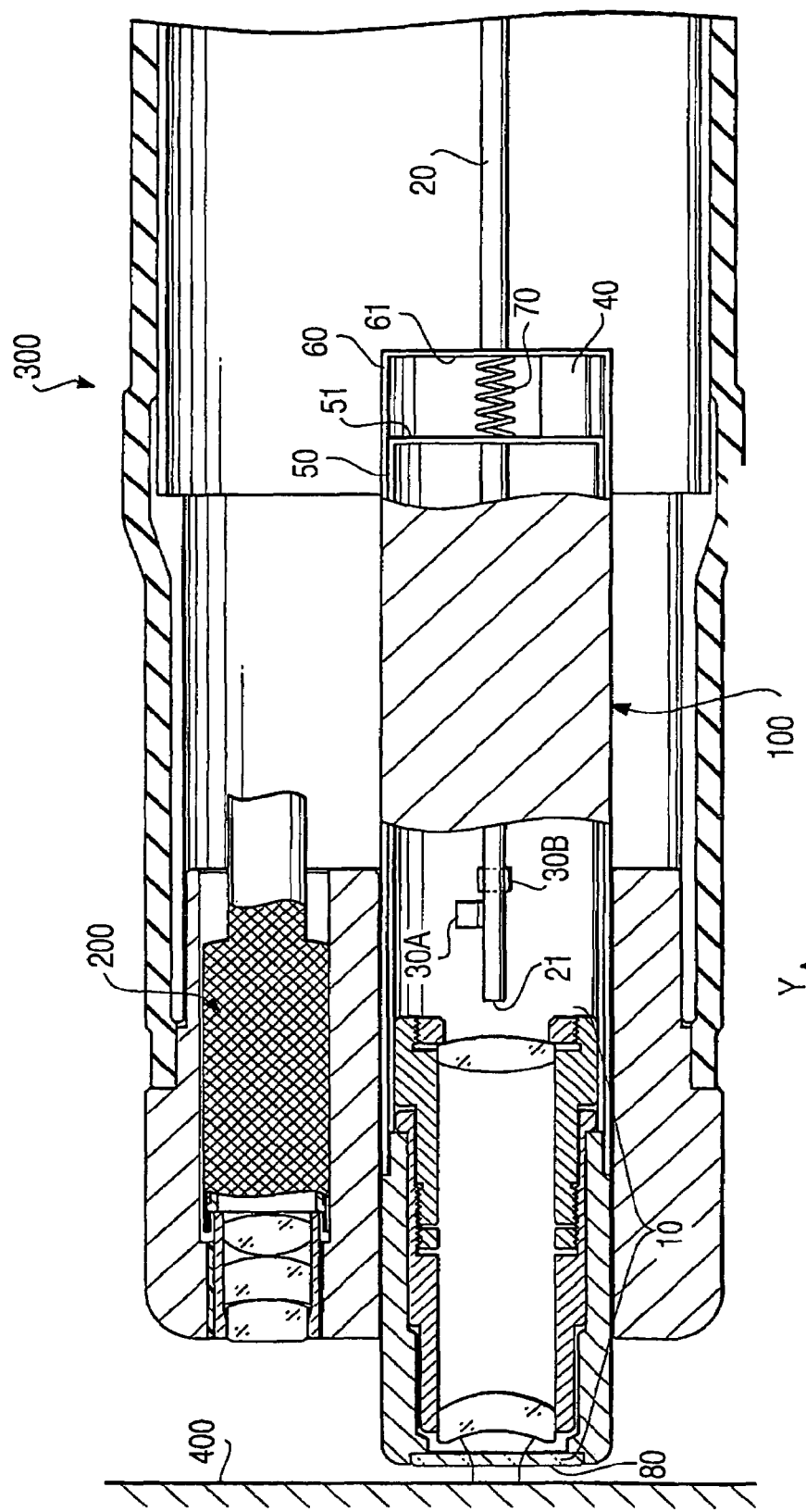
FIG. 1 is an enlarged sectional side view showing the tip of an integrated endoscope which is equipped with a confocal optical system in accordance with a first embodiment of the present invention.

Referring now to the drawings, a description will be given in detail of preferred embodiments in accordance with the present invention.

Embodiment 1

FIG. 1 is an enlarged sectional side view showing the tip of an integrated endoscope 300 which is equipped with a confocal optical system in accordance with a first embodiment of the present invention. As shown in FIG. 1, the tip of the integrated endoscope 300 includes a confocal optical system 100 which is used for observing living tissue 400 inside a body cavity of a living organism with a large magnification (confocal observation) and a general observation optical system 200 which is used for general observation of the living tissue 400. The integrated endoscope 300 is electrically and optically connected to an unshown processor which includes a light emitting unit for emitting light for illuminating the tissue 400, an image processing unit for properly processing images of the tissue 400 picked up by each of the optical systems, etc.

Although not shown in FIG. 1, the general observation optical system 200 includes an illuminating optical system for illuminating the tissue 400 with a beam supplied from the processor, an image pickup device for capturing images of the living tissue 400 illuminated by the illuminating optical system, etc.

The confocal optical system 100 includes a condensing optical system 10, a single-mode optical fiber 20 (hereinafter simply referred to as an "optical fiber 20"), piezoelectric elements 30A and 30B, a shape-memory alloy 40 and cover glass 80. The condensing optical system 10, the optical fiber 20 and the piezoelectric elements 30A and 30B are supported inside a cylindrical frame 50. The frame 50 is slidably held inside a cylindrical metal pipe 60 having a diameter slightly larger than that of the frame 50.

In the figures of this embodiment including FIG. 1, the direction of the optical axis of the condensing optical system 10 will be called a "Z direction", and two orthogonal directions that are orthogonal to the Z direction will be called an "X direction" and a "Y direction". Thus, the X direction and the Y direction defines a plane (X-Y plane) which is orthogonal to the Z direction.

The optical fiber 20 is a light guide which is provided between the light emitting unit of the processor and the condensing optical system 10. The piezoelectric elements 30A and 30B are placed in the vicinity of the emitting end 21 of the optical fiber 20 so that their displacement directions will be orthogonal to each other in an X-Y plane (X direction, Y direction). Therefore, according to voltages properly applied to the piezoelectric elements 30A and 30B, the part of the optical fiber 20 in the vicinity of the emitting end 21 is pressed and moved in the X direction and Y direction by the piezoelectric elements 30A and 30B, by which the beam emitted from the emitting end 21 scans on the surface of the tissue 400 two-dimensionally.

By letting the scanning unit move the emitting end of the optical fiber as the point source of light by bending a part of the optical fiber in the vicinity of the emitting end as above, the object (attaining a wide scan range while maintaining a small diameter of the flexible tube so that it can be applied also to an integrated endoscope) can be achieved relatively easily.

Incidentally, the locus of the emitting end of the fiber (when the part in the vicinity of the emitting end is bent as above) is not a plane in a narrow sense but a curved surface. However, by setting the distance between the center of bending and the emitting end of the fiber sufficiently long relative to the scan width of the fiber, the curved surface can be regarded substantially as a plane. In other words, the curved surface can practically be equated with a plane substantially orthogonal with the optical axis of the condensing optical system.

When a part of the optical fiber in the vicinity of the emitting end is bent as above, the emitting end face of the fiber tilts depending on the degree of bending, by which the angle between the principal ray of the beam emitted from the end face and the optical axis of the condensing optical system increases. Preferably, the condensing optical system is placed so that its entrance pupil will be at a particular point P where the optical axis of the condensing optical system intersects with an elongation of the principal ray of the beam emitted from the emitting end face. The particular intersection point P can be found easily based on the principal ray of the beam emitted from the fiber end face when the position (X, Y) of the end face on the X-Y plane (see FIGS. 1 and 2) is the most distant from the optical axis. By such placement, the beam emitted from the fiber can be taken in the condensing optical system without vignetting, etc. and thereby sufficient light quantity can be secured up to the peripheral part of the viewing field.

Between an outer wall 51 of the frame 50 and an inner wall 61 of the metal pipe 60, the shape-memory alloy 40 and a compression coil spring 70 are attached. The outer wall 51 and the inner wall 61 are substantially orthogonal to the Z-direction (i.e. on an X-Y plane). The shape-memory alloy 40 is an alloy having a shape memory function. Specifically, the shape-memory alloy 40 is deformed when external force is applied thereto at room temperatures, while it returns (contracts) to its original shape (memorized shape) when heated above a particular temperature. More specifically, the shape-memory alloy 40 is placed so as to contract in the Z direction when heated. The compression coil spring 70 is mounted between the outer wall 51 and the inner wall 61 in a compressed state (shorter than its natural length). Thus, the compression coil spring 70 constantly presses the frame 50 in the direction of the cover glass 80, that is, to the front of the endoscope.

When voltage is applied to the shape-memory alloy 40, it heats up and thereby contracts in the Z direction. The contractive force of the shape-memory alloy 40 is designed to be stronger than the compressive force of the compression coil spring 70 (tension applied to the shape-memory alloy 40 by the compression coil spring 70). Thus, the frame 50 slides in the direction opposite to the cover glass 80, that is, to the rear of the endoscope, by which the condensing position (focal point) of the beam emitted from the emitting end 21 of the optical fiber 20 and passing through the condensing optical system 10 shifts slightly in the Z direction. In other words, scanning in the Z direction becomes possible. By the functions of the piezoelectric elements 30A and 30B, the shape-memory alloy 40 and the compression coil spring 70, the confocal optical system 100 is capable of obtaining three-dimensional images (in X, Y and Z directions) of the tissue 400.

Figure 2:
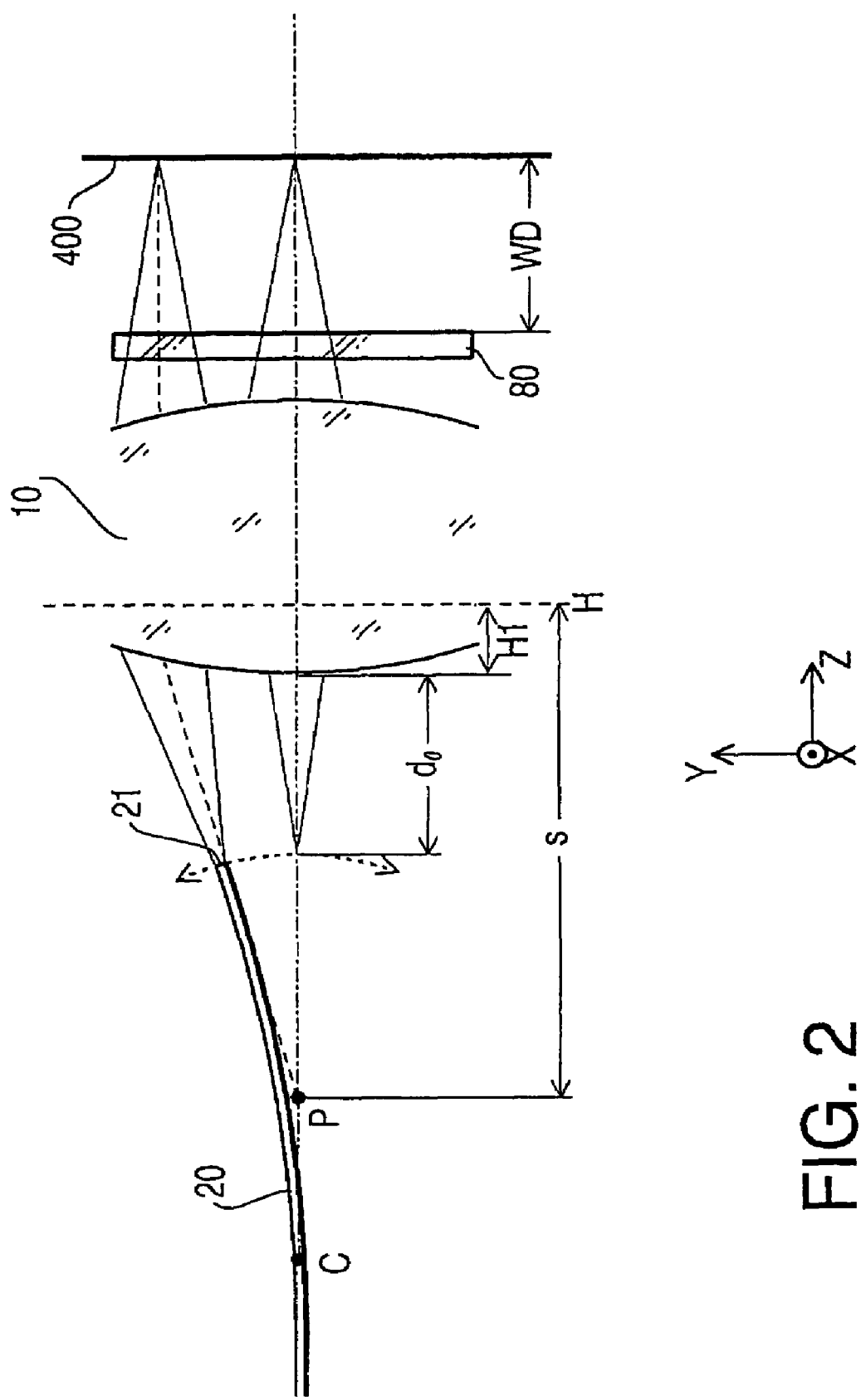
FIG. 2 is an enlarged schematic diagram showing the composition of the confocal optical system around its condensing optical system.

FIG. 2 is an enlarged schematic diagram showing the composition of the confocal optical system 100 around the condensing optical system 10. The optical fiber 20 guides the beam from the light emitting unit of the processor to the confocal optical system 100 and emits the beam from the emitting end 21. Thus, the emitting end 21 of the optical fiber 20 functions as a secondary point source of light. As mentioned above, the emitting end 21 is moved on an X-Y plane by the piezoelectric elements 30A and 30B. In the strict sense, the locus of the emitting end 21 forms a curved surface (dotted arrow) around an intersection point (center of curvature) P where the optical axis (chain line) intersects with an elongation (bold broken line) of the principal ray of the beam emitted from the emitting end 21, as shown in FIG. 2. However, the curved surface can be regarded substantially identical with the aforementioned X-Y plane since the stroke of the emitting end 21 is very small. Incidentally, as shown in FIG. 2, the intersection point (center of curvature) P is nearer to the condensing optical system 10 than a center C of bending of the optical fiber 20 which is bent by the piezoelectric elements 30A and 30B. The condensing optical system 10 is placed so that its entrance pupil will be on the intersection point P.

In the confocal optical system, it is necessary that the beam emitted from the fiber end face (moved to a prescribed position) is securely guided (returns) to the fiber end face (existing at the prescribed position) after being reflected by the subject surface. In such scanning using the reflected light from the subject surface, the reflected light can be returned to the condensing optical system with high efficiency by giving telecentricity to the subject surface side of the optical system. The beam emitted from the emitting end 21 condenses on the tissue 400 via the condensing optical system 10 and the cover glass 80, and light reflected by the tissue 400 returns to the emitting end 21 via the cover glass 80 and the condensing optical system 10. In other words, the confocal optical system 100 is configured so that the reflected light will have telecentricity.

Paraxially, the telecentricity can be attained by placing the entrance pupil at the front (fiber-side) focal position of the condensing optical system. However, at off-axis positions, the spherical aberration of the pupil gets larger and the entrance pupil for off-axis beams generally shifts from a position obtained by paraxial calculation. Thus, the condensing optical system 10 and the optical fiber 20 are placed so that the emitting end 21 will be at the front focal point of the condensing optical system 10, by which the telecentricity of the reflected light is ensured paraxially. In order to further ensure off-axis telecentricity of the reflected light, the confocal optical system 100 is configured to satisfy the following condition (5):

$$0.1 < -f/s < 1.0 \quad (5)$$

where "f" denotes a composite focal length of the whole condensing optical system 10 and "s" denotes the distance from the front principal point H of the condensing optical system 10 to the intersection point P (a direction toward the tissue 400 as a subject surface is regarded positive). The condition (5) is for securing bare minimum of telecentricity even when the off-axis beam involves the spherical aberration of the pupil. Thus, exceeding the upper limit or falling below the lower limit of the condition (5) severely deteriorates the telecentricity and causes a significant drop in the light quantity in the peripheral part.

Since the core diameter of the optical fiber 20 is extremely small, the emitting end 21 serves not only as a point source of light but also as an aperture stop. Therefore, by configuring the confocal optical system 100 to satisfy the condition (5), the emitting end 21 at a particular position receives only light that has been emitted from the emitting end 21 at the particular position and reflected at a condensing point on the tissue 400 that is optically conjugate with the emitting end 21.

The reflected light entering the emitting end 21 is guided to the processor and converted by the processor into a video signal. The video signal is outputted to a monitor, etc. and thereby images of large magnification obtained by the confocal optical system 100 are displayed.

In the above confocal optical system, three-dimensional scanning is made possible by the scanning unit and the condensing position moving unit, by which not only surface images but also tomograms of tissue in a body cavity can be obtained and observed. Further, the scanning unit scans the beam not by mirrors (as in conventional confocal optical systems) but by moving the point source of light, therefore, the whole system can be downsized. Moreover, by the employment of the condensing optical system composed as above, the beam emitted from the point source moved by the scanning unit can be condensed on the subject surface while reducing the loss of light quantity and suppressing various aberrations. By such composition of the confocal optical system, observation of tissues by wide-range, clear and sharp images becomes possible.

By the confocal optical system composed as above, the diameter of the flexible tube can be maintained small and thereby an integrated endoscope capable of reducing the load on operators can be realized.

Figure 3:
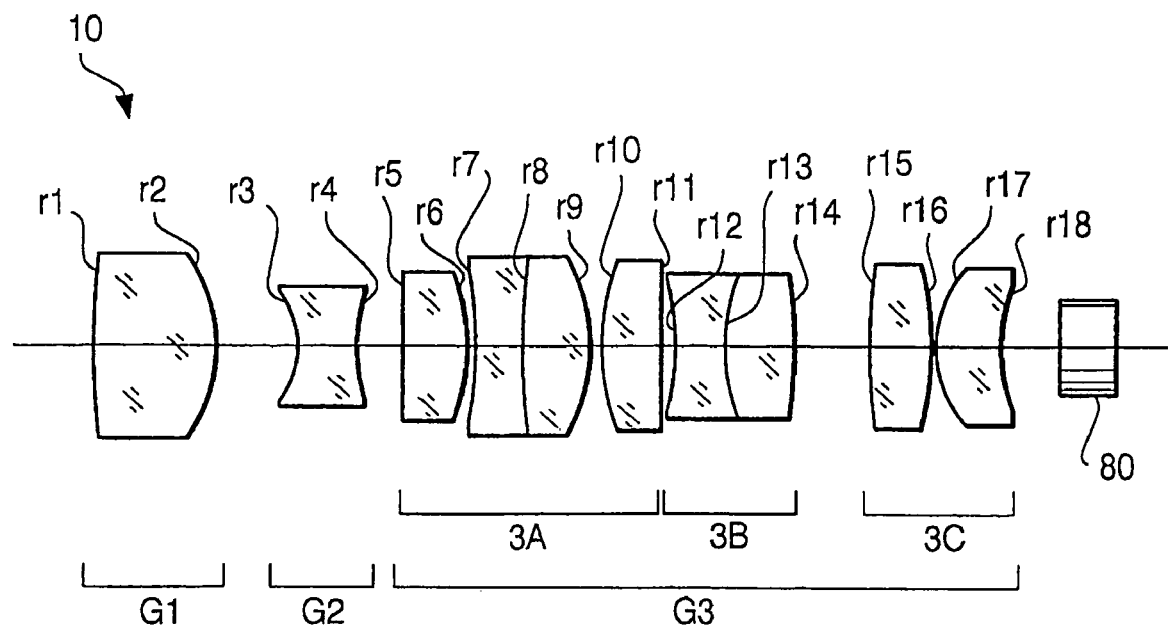
FIG. 3 is a schematic diagram showing lens arrangement of a condensing optical system as a first example of the first embodiment.

The condensing optical system 10 installed in the confocal optical system 100 composed as above will be described below in detail. FIG. 3 shows an example of lens arrangement of the condensing optical system 10.

The condensing optical system 10 includes a first group G1 having positive power, a second group G2 including at least a lens with a concave surface facing toward the cover glass 80, and a third group G3 having positive power. Although not shown in FIG. 3, the emitting end 21 of the optical fiber 20 is to the left of the first group G1. By composing the condensing optical system with such three groups, the total length of the system can be kept short.

The first group G1 in this embodiment is composed of a single lens only in order to reduce cost and weight by decreasing the number of lenses. The first group G1 having positive power functions as a condenser lens for condensing the beam (diverging beam) emitted from the emitting end 21.

The second group G2 is composed of a single lens similarly to the first group G1. The second group G2 may also be formed by a cemented lens including a positive lens and a negative lens. The concave surface r4 shown in FIG. 3 facing the cover glass 80 is mainly for keeping down the Petzval sum, and thereby has a function of correcting field curvature. Thus, the lens having the concave surface has the function of a field flattener.

The third group G3 can be further partitioned into three groups 3A, 3B and 3C. The group 3A includes a cemented lens (composed of a positive lens and a negative lens) and at least one positive lens. Incidentally, the second group diverges the beam (having a tendency to condense after passing through the first group) again. Thus, the third group is provided with positive power in order to condense the beam (after passing through the second group) again. The group 3A has positive power as a whole.

The group 3B is made of a cemented lens composed of a biconcave lens and a biconvex lens, having negative power as a whole. A strongly diverging surface r12 of the group 3B facing toward the emitting end 21 of the optical fiber 20 corrects spherical aberration. A cementing surface r13 contributes to correction of axial chromatic aberration. Incidentally, since the correction of the axial chromatic aberration might be insufficient by the cementing surface r13 only, the axial chromatic aberration correction function is also given to the first group G1 for enhancing the function. Since the first group G1 is made of a single lens as mentioned above, the axial chromatic aberration correction function can be provided to the single lens by giving the lens an Abbe number ν1 satisfying the following condition (4):

$$\nu 1 < 30 \tag{4}$$

The group 3C, having positive power as a whole, includes at least one single lens. The groups 3B and 3C are set exactly in a retrofocus configuration.

By configuring the third group as above, a working distance (WD) enough for the scanning and a high NA can be secured. The working distance means the distance between the condensing optical system and the subject surface. Specifically, the group 3A condenses the diverging beam emerging from the second group. The group 3B corrects spherical aberration of the condensing beam emerging from the group 3A, by a strong diverging surface on the point source side of a negative lens (the aforementioned biconcave lens). Further, by cementing a biconvex lens to the negative lens (biconcave lens), axial chromatic aberration is corrected satisfactorily. Here, the power of the group 3A alone does not have a condensing effect enough for attaining a high NA, therefore, the group 3C having positive power is provided in order to condense the beam enough. Incidentally, the groups 3B and 3C are configured in the so-called retrofocus type, by which a sufficient working distance is secured.

The condensing optical system 10 is configured to satisfy the following condition (1):

$$0.1 < |m \times NA| < 0.2 \tag{1}$$

where "m" denotes magnification of the condensing optical system 10 and "NA" denotes a numerical aperture on the subject surface side of the condensing optical system 10.

The condition (1) specifies the relationship between a scan range attained by moving the point source of light and the numerical aperture NA of the condensing optical system on its subject surface side. Specifically, when the value |m×NA| falls below the lower limit, the numerical aperture becomes insufficient and thereby attaining enough resolution becomes impossible. Meanwhile, when the value exceeds the upper limit, the numerical aperture becomes too large and the correction of spherical aberration becomes difficult. Further, the magnification becomes too small and securing a sufficient scan range becomes difficult. Thus, the condensing optical system satisfying the condition (1) is suitable for the composition which scans the beam spot on the subject surface by swinging the point source of light inside the flexible tube endoscope having a limited space therein.

The condensing optical system 10 satisfying the condition (1) is capable of emitting the beam (emerging from the emitting end 21) from the tip of the flexible tube and condensing the beam on the subject surface while minimizing loss of light quantity and suppressing aberrations.

Further, the condensing optical system 10 is composed to satisfy the following conditions (2) and (3):

$$0.1 < d0/f1 < 0.5 \tag{2}$$

$$0.2 < |f1/f| < 2.0 \tag{3}$$

where "d0" denotes the distance from the emitting end 21 to the first surface r1 of the condensing optical system 10, "f" denotes the composite focal length of the whole condensing optical system 10, and "f1" denotes the focal length of the first group G1.

The point source of light constantly moves for scanning the beam. Meanwhile, the beam emitted from the point source originally diverges, that is, spreads (diverges) wider as the distance from the point source becomes longer. In the condensing optical system, the beam diverging is condensed by the first group which is placed just after the point source. Therefore, the diameter of the lens of the first group can be reduced and the whole condensing optical system can be miniaturized further as the first group is placed nearer to the point source. However, placing the first group too close to the point source might cause contact of the lens of the first group with the point source which is moving. The condition (2) specifies such a positional relationship between the point source of light and the first group and the miniaturization of the condensing optical system. The miniaturization becomes difficult when the value d0/f1 exceeds the upper limit of the condition (2), while the first group makes contact with the point source when the value falls below the lower limit.

As mentioned above, the first group has positive power for condensing the diverging beam emitted from the point source. The condition (3) is for properly setting the power of the first group, considering power balance with the power of the whole system. When the value |f1/f| falls below the lower limit of the condition (3), the power of the first group becomes too strong, by which distortion might be caused. When the value exceeds the upper limit, the power of the first group becomes too weak, causing an exceedingly large diameter of the lens forming the first group.

By satisfying both the conditions (2) and (3), the condensing optical system 10 is allowed to suppress various aberrations (distortion, etc.) satisfactorily while being miniaturized.

In the following, four concrete examples of the condensing optical system 10 in accordance to the first embodiment of the present invention will be described in detail.

EXAMPLE 1-1

FIG. 3 is a schematic diagram showing lens arrangement of a condensing optical system 10 as a first example of the first embodiment. The following Table 1 shows specific numerical configuration of the condensing optical system 10 of the first example.

TABLE 1

| No. | r | d | n | ν | REMARKS |
|---|---|---|---|---|---|
| 0 |  | 0.566 |  |  | EMITTING END 21 |
| 1 | 20.605 | 1.388 | 1.84666 | 23.8 | G1 |
| 2 | −2.371 | 0.932 |  |  |  |
| 3 | −1.377 | 0.652 | 1.51633 | 64.1 | G2 |
| 4 | 2.251 | 0.539 |  |  |  |
| 5 | 65.406 | 0.733 | 1.77250 | 49.6 | G3 (3A) |
| 6 | −3.343 | 0.109 |  |  |  |
| 7 | −5.097 | 0.543 | 1.84666 | 23.8 |  |
| 8 | 8.772 | 0.790 | 1.72000 | 50.2 |  |
| 9 | −2.449 | 0.130 |  |  |  |
| 10 | 3.402 | 0.687 | 1.74950 | 35.3 |  |
| 11 | 248.843 | 0.143 |  |  |  |
| 12 | −4.131 | 0.572 | 1.84666 | 23.8 | G3 (3B) |

TABLE 1-continued

| No. | r | d | n | v | REMARKS |
|---|---|---|---|---|---|
| 13 | 2.789 | 0.800 | 1.62230 | 53.2 | |
| 14 | −9.924 | 0.837 | | | |
| 15 | 11.211 | 0.722 | 1.77250 | 49.6 | G3 (3C) |
| 16 | −4.263 | 0.046 | | | |
| 17 | 1.737 | 0.744 | 1.88300 | 40.8 | |
| 18 | 2.696 | 0.662 | | | |
| 19 | ∞ | 0.687 | 1.51633 | 64.1 | COVER GLASS 80 |
| 20 | ∞ | — | | | |

In Table 1, "No." denotes the surface number, "r" denotes the curvature radius [mm] of each lens surface, "d" denotes the lens thickness or lens interval [mm], "n" denotes the refractive index at the D line wavelength (588 nm), "v" denotes the Abbe number at the D line wavelength, and "REMARKS" denotes the optical element indicated by each surface number (ditto for following tables).

EXAMPLE 1-2

Figure 4:
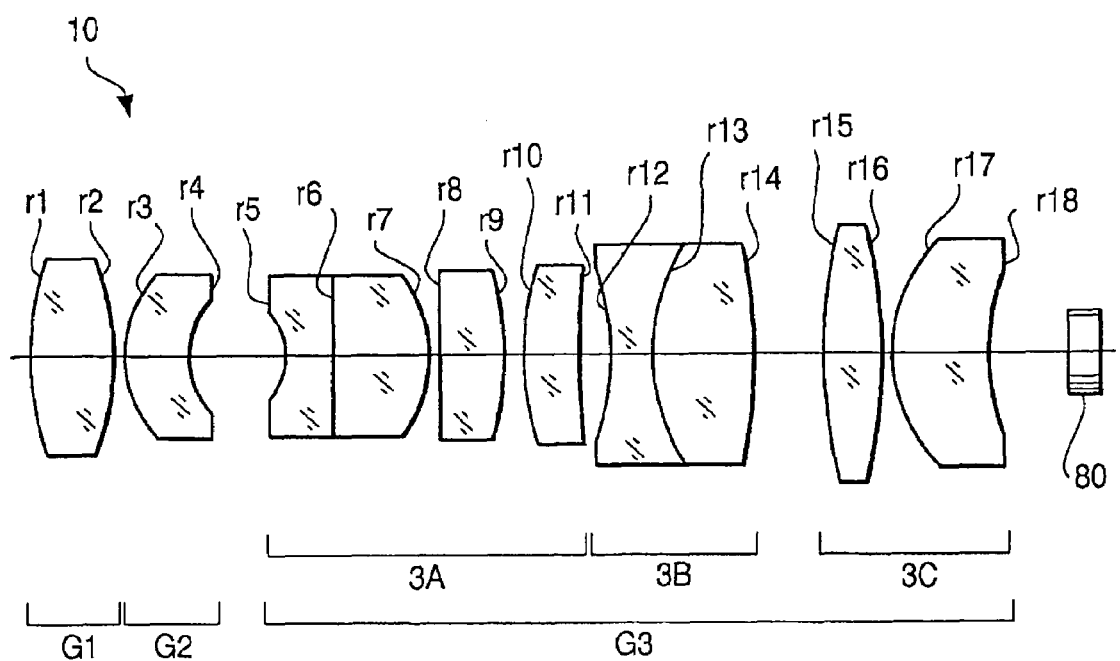
FIG. 4 is a schematic diagram showing lens arrangement of a condensing optical system as a second example of the first embodiment.

FIG. 4 is a schematic diagram showing lens arrangement of a condensing optical system 10 as a second example of the first embodiment. The following Table 2 shows specific numerical configuration of the condensing optical system 10 of the second example.

TABLE 2

| No. | r | d | n | v | REMARKS |
|---|---|---|---|---|---|
| 0 | | 0.900 | | | EMITTING END 21 |
| 1 | 5.242 | 1.064 | 1.92286 | 18.9 | G1 |
| 2 | −4.231 | 0.128 | | | |
| 3 | 1.812 | 0.795 | 1.51633 | 64.1 | G2 |
| 4 | 1.228 | 1.269 | | | |
| 5 | −0.991 | 0.577 | 1.84666 | 23.8 | G3 (3A) |
| 6 | 244.027 | 1.218 | 1.77250 | 49.6 | |
| 7 | −2.035 | 0.128 | | | |
| 8 | −73.520 | 0.833 | 1.77250 | 49.6 | |
| 9 | −5.049 | 0.256 | | | |
| 10 | 4.564 | 0.744 | 1.88300 | 40.8 | |
| 11 | 13.138 | 0.397 | | | |
| 12 | −3.900 | 0.513 | 1.84666 | 23.8 | G3 (3B) |
| 13 | 2.914 | 1.282 | 1.74400 | 44.8 | |
| 14 | −7.963 | 0.885 | | | |
| 15 | 7.987 | 0.756 | 1.88300 | 40.8 | G3 (3C) |
| 16 | −7.987 | 0.128 | | | |
| 17 | 2.350 | 1.231 | 1.88300 | 40.8 | |
| 18 | 3.095 | 1.030 | | | |
| 19 | ∞ | 0.385 | 1.51633 | 64.1 | COVER GLASS 80 |
| 20 | ∞ | — | | | |

EXAMPLE 1-3

Figure 5:
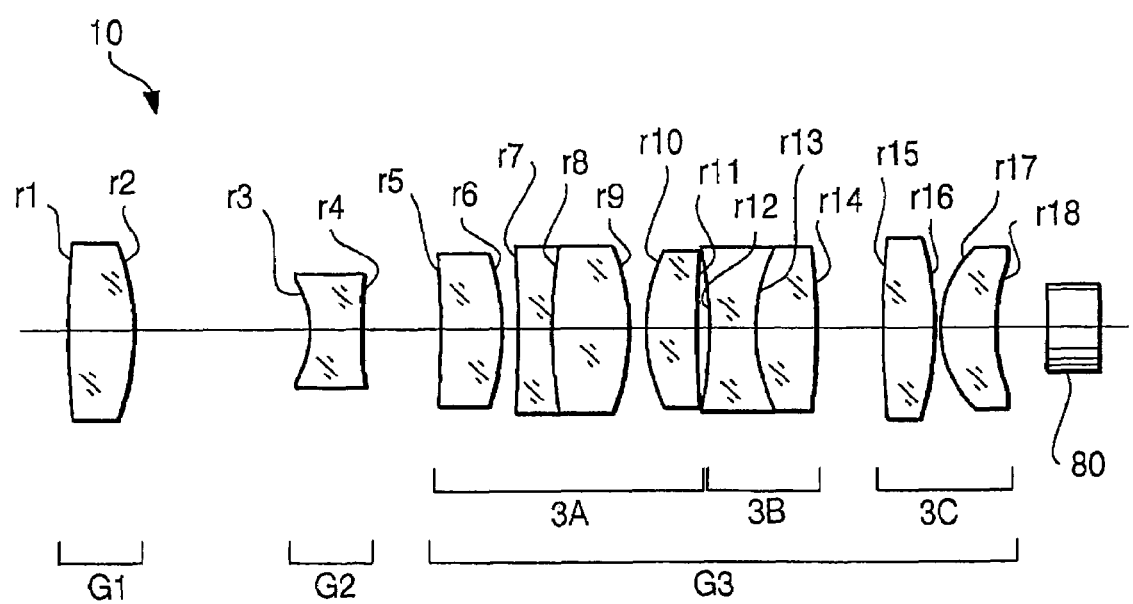
FIG. 5 is a schematic diagram showing lens arrangement of a condensing optical system as a third example of the first embodiment.

FIG. 5 is a schematic diagram showing lens arrangement of a condensing optical system 10 as a third example of the first embodiment. The following Table 3 shows specific numerical configuration of the condensing optical system 10 of the third example.

TABLE 3

| No. | r | d | n | v | REMARKS |
|---|---|---|---|---|---|
| 0 | | 0.499 | | | EMITTING END 21 |
| 1 | 16.174 | 0.800 | 1.84666 | 23.8 | G1 |
| 2 | −3.186 | 2.099 | | | |

TABLE 3-continued

| No. | r | d | n | v | REMARKS |
|---|---|---|---|---|---|
| 3 | −1.235 | 0.600 | 1.51633 | 64.1 | G2 |
| 4 | 5.044 | 0.980 | | | |
| 5 | −17.209 | 0.750 | 1.77250 | 49.6 | G3 (3A) |
| 6 | −3.417 | 0.200 | | | |
| 7 | −11.114 | 0.400 | 1.84666 | 23.8 | |
| 8 | 7.125 | 0.900 | 1.72000 | 50.2 | |
| 9 | −3.530 | 0.200 | | | |
| 10 | 3.130 | 0.632 | 1.74950 | 35.3 | |
| 11 | 228.926 | 0.132 | | | |
| 12 | −3.800 | 0.526 | 1.84666 | 23.8 | G3 (3B) |
| 13 | 2.566 | 0.736 | 1.62230 | 53.2 | |
| 14 | −9.130 | 0.770 | | | |
| 15 | 10.314 | 0.664 | 1.77250 | 49.6 | G3 (3C) |
| 16 | −3.922 | 0.042 | | | |
| 17 | 1.598 | 0.684 | 1.88300 | 40.8 | |
| 18 | 2.480 | 0.600 | | | |
| 19 | ∞ | 0.632 | 1.51633 | 64.1 | COVER GLASS 80 |
| 20 | ∞ | — | | | |

EXAMPLE 1-4

Figure 6:
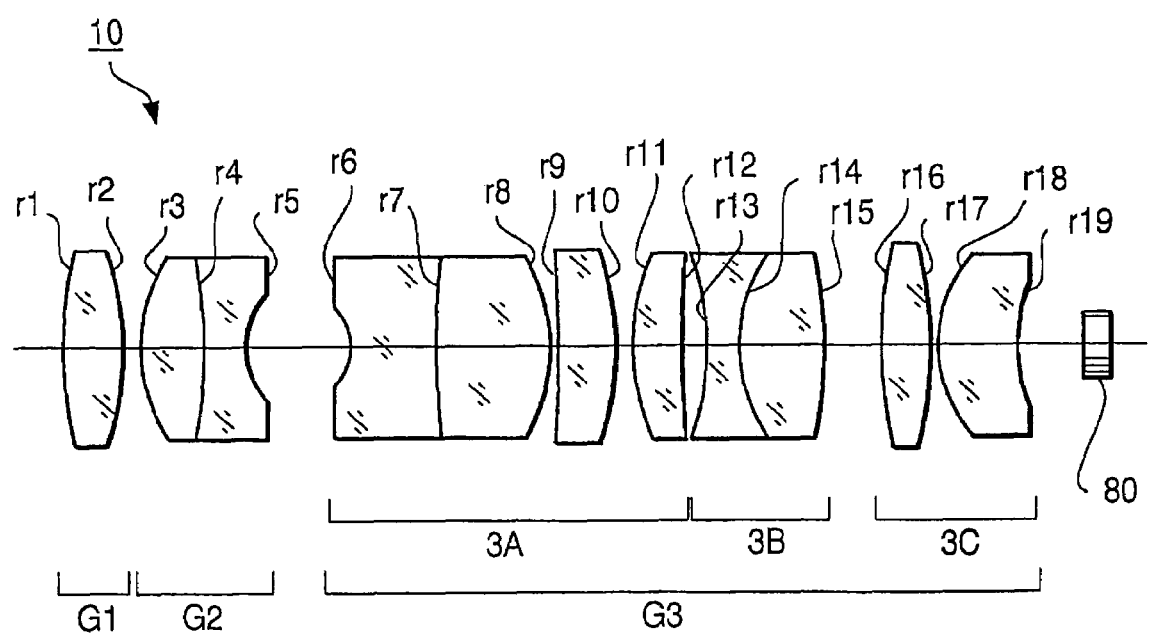
FIG. 6 is a schematic diagram showing lens arrangement of a condensing optical system as a fourth example of the first embodiment.
Figure 7:
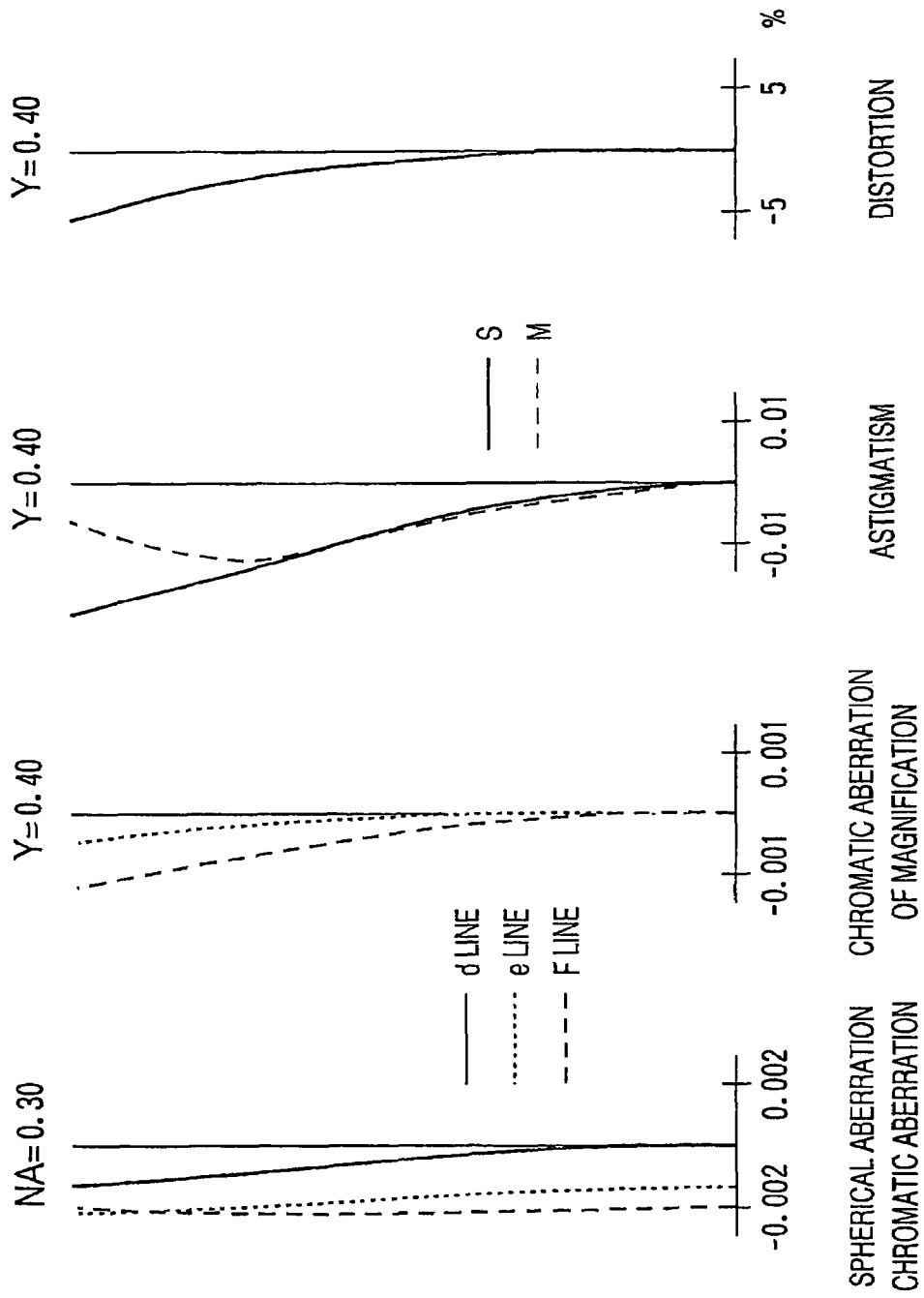
FIGS. 7A through 7D are graphs showing aberrations occurring in the condensing optical system of the first example of the first embodiment.
Figure 8:
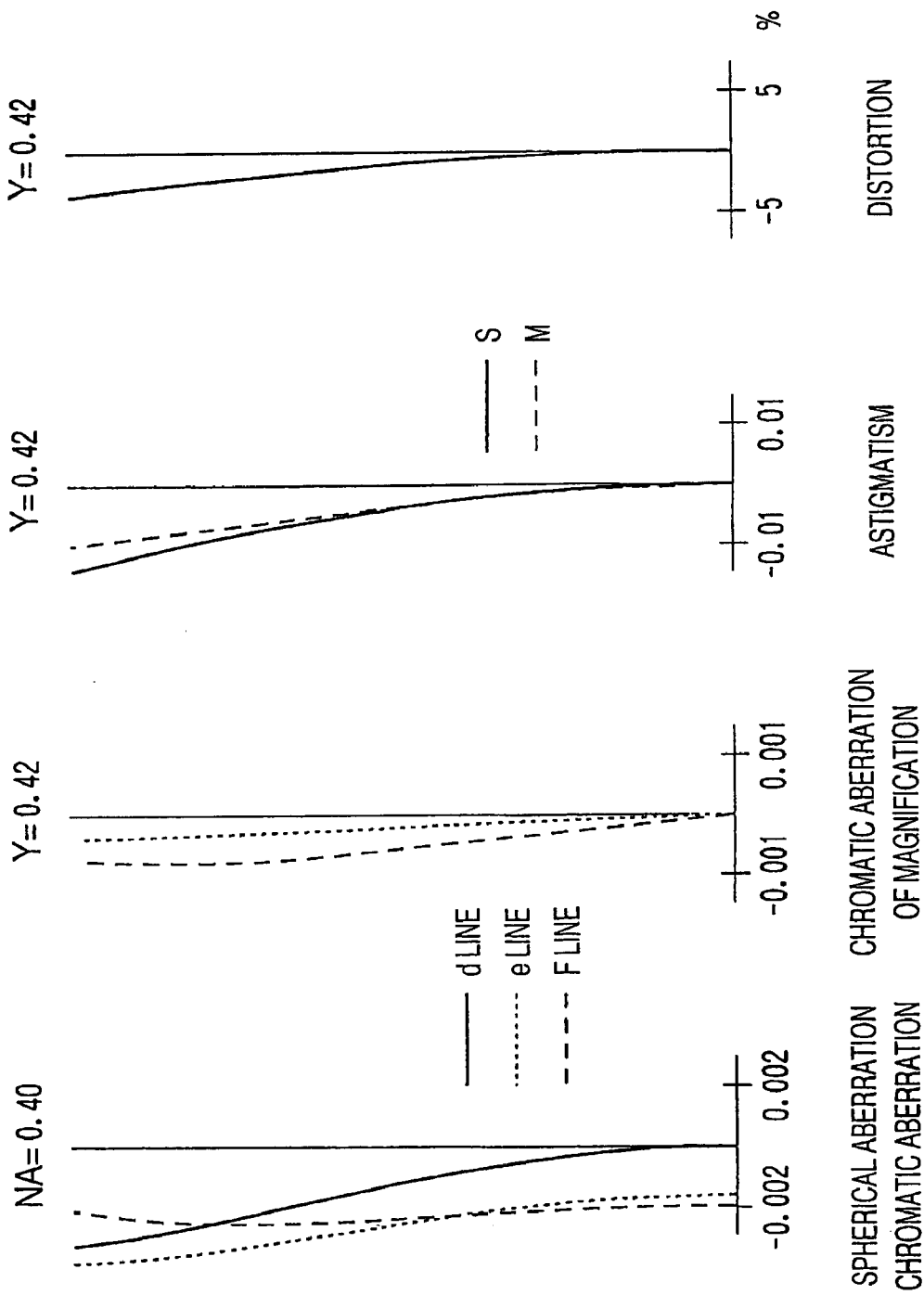
FIGS. 8A through 8D are graphs showing aberrations occurring in the condensing optical system of the second example of the first embodiment.
Figure 9:
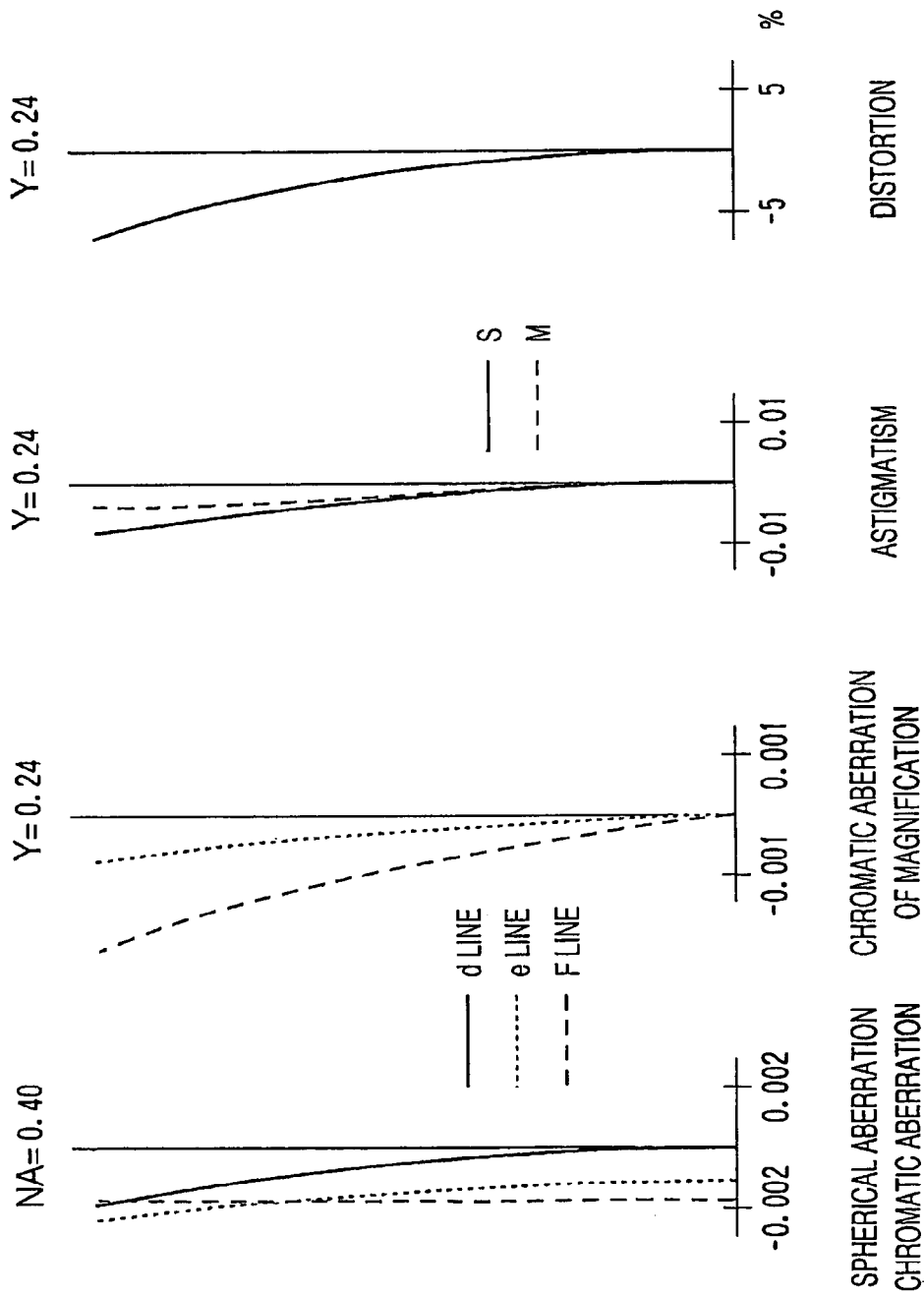
FIGS. 9A through 9D are graphs showing aberrations occurring in the condensing optical system of the third example of the first embodiment.
Figure 10:
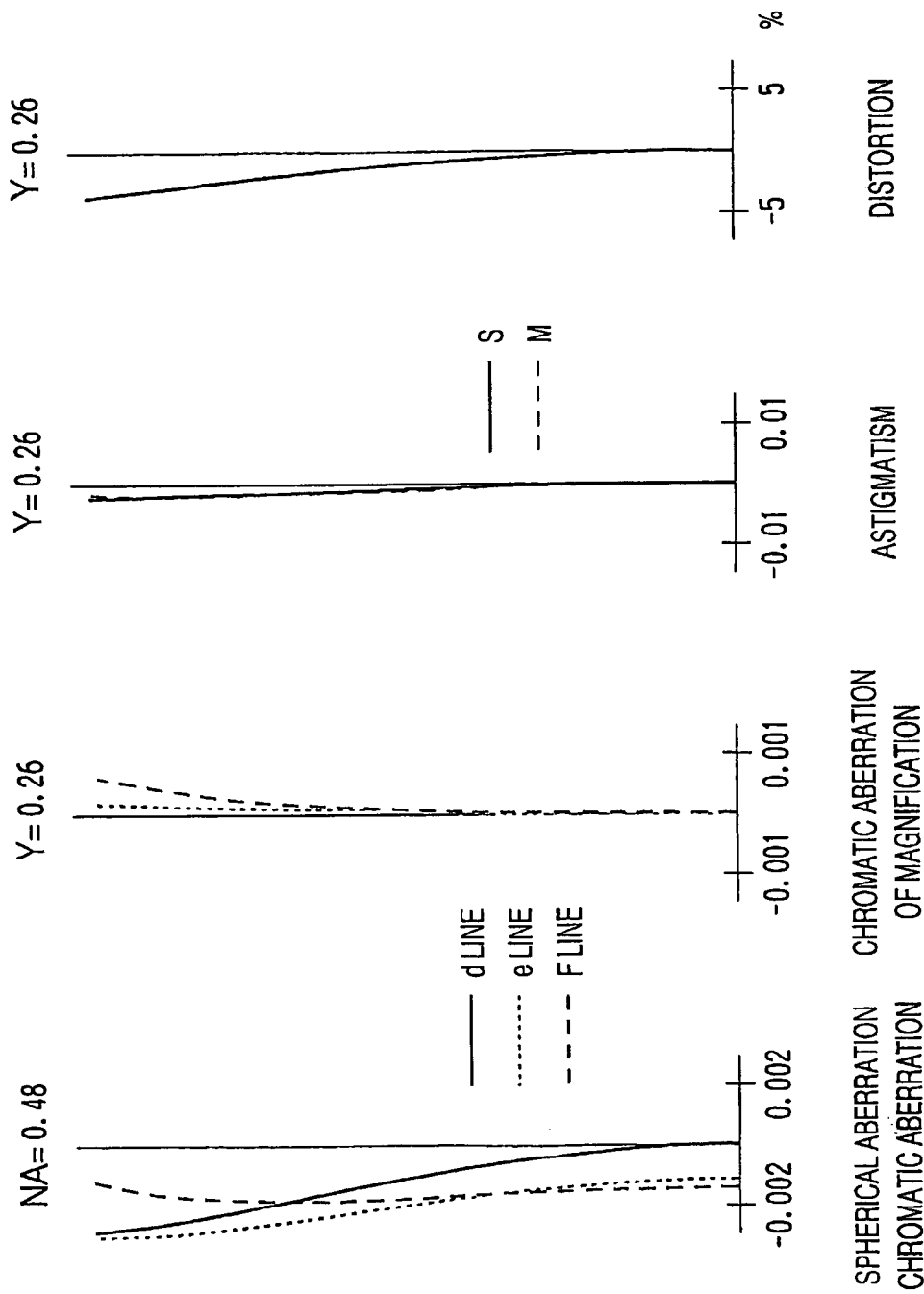
FIGS. 10A through 10D are graphs showing aberrations occurring in the condensing optical system of the fourth example of the first embodiment.

FIG. 6 is a schematic diagram showing lens arrangement of a condensing optical system 10 as a fourth example of the first embodiment. The following Table 4 shows specific numerical configuration of the condensing optical system 10 of the fourth example.

TABLE 4

| No. | r | d | n | v | REMARKS |
|---|---|---|---|---|---|
| 0 | | 0.566 | | | EMITTING END 21 |
| 1 | 6.768 | 0.697 | 1.92286 | 18.9 | G1 |
| 2 | −4.414 | 0.210 | | | |
| 3 | 2.554 | 0.758 | 1.84666 | 23.8 | G2 |
| 4 | −6.519 | 0.458 | 1.51633 | 64.1 | |
| 5 | 1.117 | 1.236 | | | |
| 6 | −0.876 | 1.047 | 1.84666 | 23.8 | G3 (3A) |
| 7 | 11.986 | 1.398 | 1.77250 | 49.6 | |
| 8 | −2.407 | 0.100 | | | |
| 9 | −24.305 | 0.701 | 1.77250 | 49.6 | |
| 10 | −4.439 | 0.200 | | | |
| 11 | 3.560 | 0.576 | 1.88300 | 40.8 | |
| 12 | 10.241 | 0.306 | | | |
| 13 | −3.042 | 0.400 | 1.84666 | 23.8 | G3 (3B) |
| 14 | 2.273 | 1.009 | 1.74400 | 44.8 | |
| 15 | −6.211 | 0.689 | | | |
| 16 | 6.231 | 0.586 | 1.88300 | 40.8 | G3 (3C) |
| 17 | −6.231 | 0.100 | | | |
| 18 | 1.833 | 0.956 | 1.88300 | 40.8 | |
| 19 | 2.414 | 0.783 | | | |
| 20 | ∞ | 0.300 | 1.51633 | 64.1 | COVER GLASS 80 |
| 21 | ∞ | — | | | |

As shown in FIGS. 3 through 6, in the first through fourth examples of the first embodiment, the first group G1 is composed of a single lens only in order to reduce the weight of the condensing optical system 10 by decreasing the number of lenses. While the second group G2 is composed of one single lens in the first through third examples, the fourth example employs a cemented lens and thereby copes with a high NA 0.48. In each example, the group 3A includes two positive single lenses. The group 3C composed of a biconvex lens and a positive meniscus lens. By the distribution of positive power to two or more single lenses, spherical aberration and coma, occurring when a spherical lens is used for the group 3A or 3C, are suppressed well.

The following Table 5 shows the values included in the expressions of the aforementioned conditions (1)-(5) regarding the condensing optical systems 10 of the first through fourth examples of the first embodiment. In Table 5, "H1" denotes the distance from the first surface r1 to the front principal point H. The values of the expressions of the conditions (1)-(5) obtained by substituting the values of Table 5 into the expressions will be shown in Table 6.

TABLE 5

|    | EX. 1   | EX. 2   | EX. 3   | EX. 4  |
|----|---------|---------|---------|--------|
| m  | −0.422  | −0.438  | −0.265  | −0.266 |
| NA | 0.30    | 0.40    | 0.40    | 0.48   |
| f  | 6.664   | −4.564  | −10.650 | −1.703 |
| f1 | 2.583   | 2.682   | 3.205   | 2.984  |
| d0 | 0.545   | 0.900   | 0.499   | 0.566  |
| ν1 | 23.9    | 18.9    | 23.9    | 18.9   |
| s  | −38.737 | 7.277   | 35.859  | 3.618  |
| H1 | 21.8928 | −15.8773| −51.3578| −8.6841|

TABLE 6

| CONDITION | EX. 1 | EX. 2 | EX. 3 | EX. 4 |
|-----------|-------|-------|-------|-------|
| (1)       | 0.127 | 0.175 | 0.106 | 0.128 |
| (2)       | 0.211 | 0.336 | 0.156 | 0.190 |
| (3)       | 0.388 | 0.588 | 0.301 | 1.752 |
| (4)       | 23.9  | 18.9  | 23.9  | 18.9  |
| (5)       | 0.172 | 0.627 | 0.297 | 0.471 |

FIGS. 7A through 10D are graphs showing aberrations occurring in the condensing optical systems 10 of the first through fourth examples of the first embodiment, in which FIGS. 7A, 8A, 9A and 10A show spherical aberration and axial chromatic aberration, FIGS. 7B, 8B, 9B and 10B show chromatic aberration of magnification, FIGS. 7C, 8C, 9C and 10C show astigmatism, and FIGS. 7D, 8D, 9D and 10D show distortion. In the graphs 7A, 8A, 9A and 10A showing spherical aberration and axial chromatic aberration, "E line" denotes a wavelength 546 nm and "F line" denotes a wavelength 486 nm. In the graphs 7C, BC, 9C and 10C showing astigmatism, "S" denotes sagittal and "M" denotes meridional. Each of the first through fourth examples satisfies all the conditions (1)-(5) as shown in Table 6. Therefore, the aberrations are all suppressed excellently in the condensing optical systems 10 of the first through fourth examples of the first embodiment.

As described above, by the first embodiment in accordance with the present invention, a condensing optical system suitable for a confocal optical system (implementing the three-dimensional scanning by swinging the point source of light) and capable of satisfactorily suppressing various aberrations and reducing loss of light quantity is obtained. The confocal optical system equipped with such a condensing optical system can be formed small in size while securing a wide scan range. By use of such a confocal optical system, an integrated endoscope with a thin flexible tube can be realized.

Embodiment 2

Figure 11:
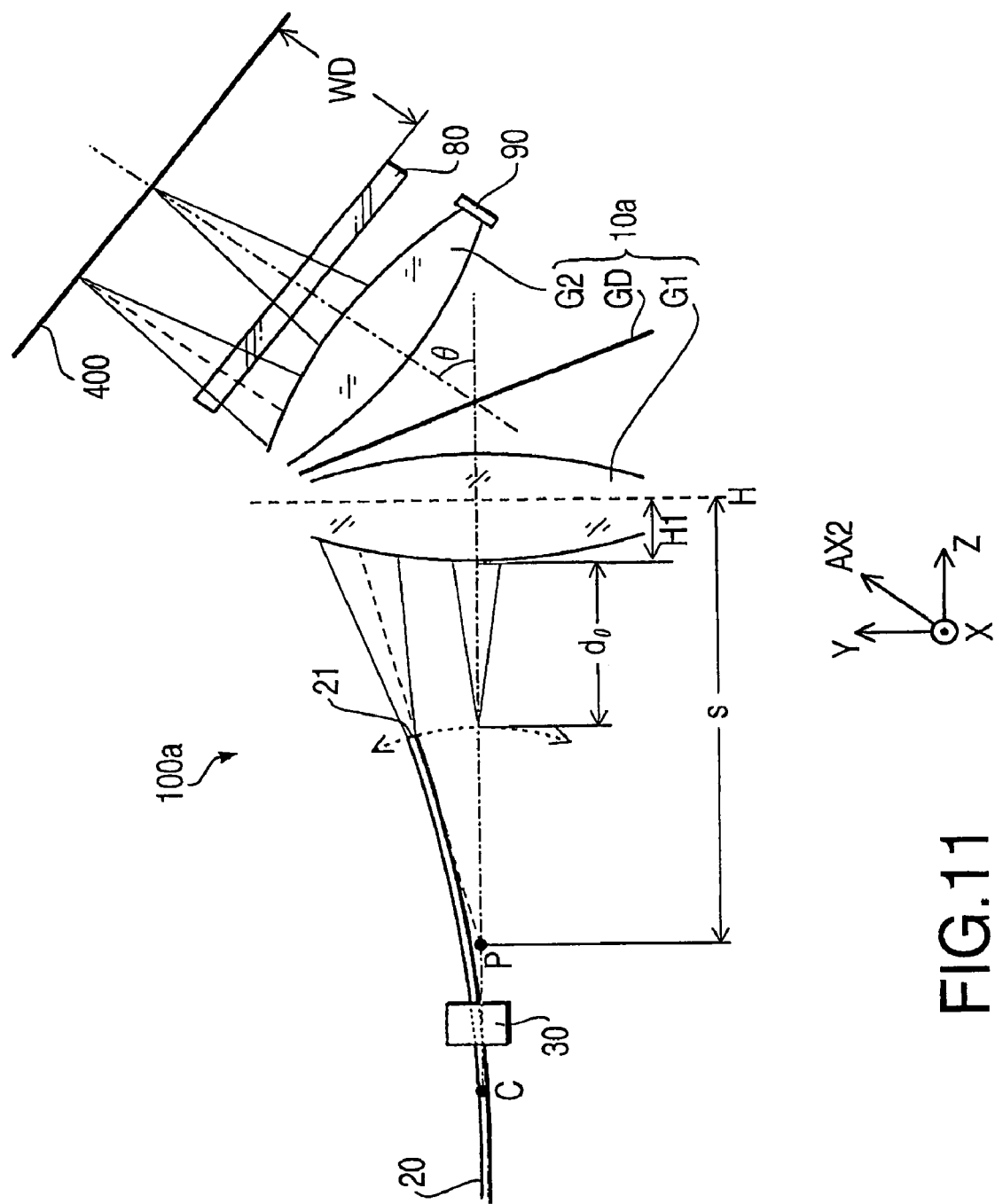
FIG. 11 is an enlarged schematic diagram showing the composition of a confocal optical system in accordance with a second embodiment of the present invention around its condensing optical system.

FIG. 11 is an enlarged schematic diagram showing the composition of a confocal optical system 100a in accordance with a second embodiment of the present invention around its condensing optical system 10a. While the confocal optical system 100 of the first embodiment was installed in the integrated endoscope 300 of a direct view type, the confocal optical system 100a of the second embodiment is installed in an integrated endoscope of a lateral view type (including a lateral view optical system) for observing living tissue 400 in a body cavity with a large magnification. The lateral view integrated endoscope also includes a general observation optical system (unshown) which is used for general observation of the living tissue 400, similarly to the direct view integrated endoscope 300 explained in the first embodiment. The lateral view integrated endoscope is electrically and optically connected to an unshown processor which includes a light emitting unit for emitting light for illuminating the tissue 400, an image processing unit for properly processing images of the tissue 400 picked up by each of the optical systems, etc.

The confocal optical system 100a includes a condensing optical system 10a, a single-mode optical fiber 20 (hereinafter simply referred to as an "optical fiber 20"), a cover glass 80, a fiber end driver 30 and a lens driver 90. The condensing optical system 10a includes a first group G1 (nearest to the emitting end 21 of the optical fiber 20), a deflecting group GD, and a second group G2. The optical fiber 20, the fiber end driver 30, the first group G1, the deflecting group GD and the cover glass 80 are fixed inside the confocal optical system 100a. The second group G2 is held by the lens driver 90 to be slidable in the direction of the optical axis of the second group G2. By pressing the cover glass against the subject surface, a proper distance can be secured between the condensing position (inside the subject) and the subject surface. Therefore, by at least changing the distance between the second group and the cover glass by moving the second group in the optical axis direction, the condensing position can be moved in the optical axis direction (i.e. in the depth direction of the subject).

In the figures of this embodiment including FIG. 11, the direction of the installation of the optical fiber 20 (the direction of the optical axis of the first group G1) will be called a "Z direction", and two orthogonal directions that are orthogonal to the Z direction will be called an "X direction" and a "Y direction". Thus, the X direction and the Y direction defines a plane (X-Y plane) which is orthogonal to the Z direction. For convenience of explanation, the direction of the optical axis of the second group G2 will be called an "AX2 direction". Incidentally, some descriptions in this specification are given assuming an imaginary state in which the optical axis of the condensing optical system is developed into a straight line as needed for the sake of convenience.

The optical fiber 20 is a light guide which is provided between the light emitting unit of the processor and the condensing optical system 10a. The fiber end driver 30 is placed in the vicinity of the emitting end 21 of the optical fiber 20. The fiber end driver 30 includes two piezoelectric elements 30A and 30B whose displacement directions are orthogonal to each other in an X-Y plane (X direction, Y direction). Therefore, according to voltages properly applied to the piezoelectric elements of the fiber end driver 30, the part of the optical fiber 20 in the vicinity of the emitting end 21 is pressed and moved in the X direction and Y direction by the fiber end driver 30, by which the beam emitted from the emitting end 21 scans on the surface of the tissue 400 two-dimensionally.

Further, the lens driver 90 drives the second group G2 in the AX2 direction, by which the condensing position (focal point) of the beam emitted from the emitting end 21 of the optical fiber 20 and passing through the condensing optical system 10a shifts slightly in the AX2 direction. In other words, scanning in the AX2 direction becomes possible. By the functions of the fiber end driver 30 and the lens driver 90, the confocal optical system 100a is capable of obtaining three-dimensional images (in X, Y and AX2 directions) of the tissue 400.

The optical fiber 20 guides the beam from the light-emitting unit of the processor to the confocal optical system 100a and emits the beam from the emitting end 21. Thus, the emitting end 21 of the optical fiber 20 functions as a secondary point source of light. As mentioned above, the emitting end 21 is moved on the X-Y plane by the fiber end driver 30. In the strict sense, the locus of the emitting end 21 forms a curved surface (dotted arrow) around an intersection point (center of curvature) P where the optical axis (chain line) intersects with an elongation (bold broken line) of the principal ray of the beam emitted from the emitting end 21, as shown in FIG. 11. However, the curved surface can be regarded substantially identical with the X-Y plane since the stroke of the emitting end 21 is very small. Incidentally, as shown in FIG. 11, the intersection point (center of curvature) P is nearer to the condensing optical system 10a than a center C of bending of the optical fiber 20 which is bent by the fiber end driver 30. The first group G1 of the condensing optical system 10a is placed so that its entrance pupil will be at the intersection point P.

The beam emitted from the emitting end 21 condenses on the tissue 400 via the condensing optical system 10a and the cover glass 80, and light reflected by the tissue 400 returns to the emitting end 21 via the cover glass 80 and the condensing optical system 10a In other words, the confocal optical system 100a is configured so that the reflected light from the tissue 400 will have telecentricity. Thus, the condensing optical system 10a and the optical fiber 20 are placed so that the emitting end 21 will be at the front focal point of the condensing optical system 10a, by which the telecentricity of the reflected light is ensured paraxially. In order to further ensure off-axis telecentricity of the reflected light, the confocal optical system 100a is configured to satisfy the following condition (7a):

$$0.1 < -f/s < 1.0 \tag{7a}$$

where "f" denotes a composite focal length of the whole condensing optical system 10a and "s" denotes the distance from the front principal point H of the condensing optical system 10a to the intersection point P (a direction toward the tissue 400 as a subject surface is regarded positive).

Since the core diameter of the optical fiber 20 is extremely small, the emitting end 21 serves not only as a point source of light but also as an aperture stop. Therefore, by configuring the confocal optical system 100a to satisfy the condition (7a), the emitting end 21 at a particular position receives only light that has been emitted from the emitting end 21 at the particular position and reflected at a condensing point on the tissue 400 that is optically conjugate with the emitting end 21.

The reflected light entering the emitting end 21 is guided to the processor and converted by the processor into a video signal. The video signal is outputted to a monitor, etc. and thereby images of large magnification obtained by the confocal optical system 100 are displayed.

In the above confocal optical system, three-dimensional scanning is made possible by the scanning unit and the condensing position moving unit, by which not only surface images but also tomograms of tissue in a body cavity can be obtained and observed. Further, the scanning unit scans the beam not by mirrors (as in conventional confocal optical systems) but by moving the point source of light, therefore, the whole system can be downsized. Moreover, by the employment of the condensing optical system composed as above, the beam emitted from the point source moved by the scanning unit can be condensed on the subject surface while reducing the loss of light quantity and suppressing various aberrations. By such composition of the confocal optical system, observation of tissues by wide-range, clear and sharp images becomes possible.

By the confocal optical system of the lateral view type composed as above, the diameter of the flexible tube can be maintained small and thereby an integrated endoscope of a lateral view type, capable of reducing the load on operators, can be realized.

Figure 12:
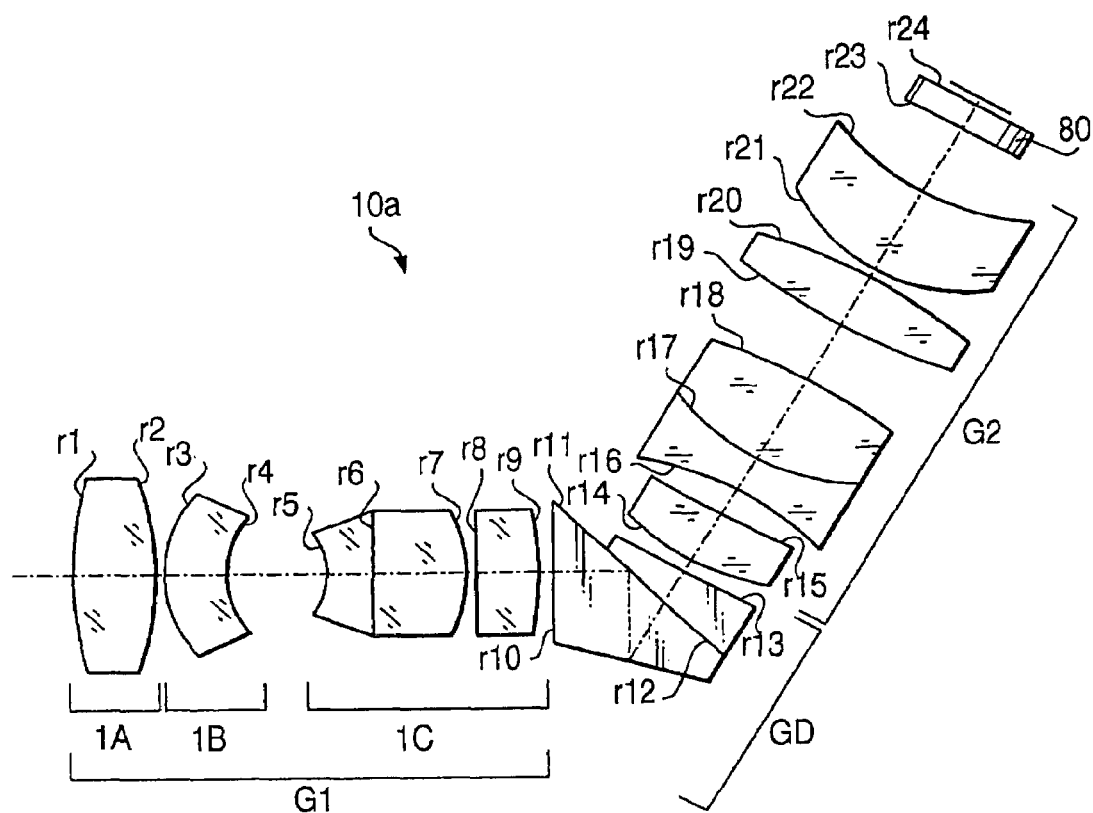
FIG. 12 is a schematic diagram showing lens arrangement of a condensing optical system as a first example of the second embodiment.

The condensing optical system 10a installed in the confocal optical system 100a composed as above will be described below in detail. FIG. 12 shows an example of lens arrangement of the condensing optical system 10a.

In the condensing optical system 10a, the first group G1 includes a group 1A having positive power, a group 1B including a single lens or cemented lens with at least a concave surface facing toward the cover glass 80, and a group 1C composed of a cemented lens and a single lens. Although not shown in FIG. 12, the emitting end 21 of the optical fiber 20 is to the left of the group 1A.

Specifically, the group 1A condenses the diverging beam emitted from the point source of light by its positive power, that is, the group 1A has the function of a condenser lens. The concave surface of the group 1B is mainly for keeping down the Petzval sum, by which field curvature is corrected. Thus, the lens having the concave surface has the function of a field flattener. Incidentally, the group 1B diverges the beam (having a tendency to condense after passing through the group 1A) again. Thus, the group 1C is provided with positive power in order to prevent the beam (after passing through the group 1B) from diverging. By composing the condensing optical system as above, the total length of the system can be kept short.

While the group 1A can be formed of two or more lenses, the group 1A in this embodiment is composed of a single lens only in order to reduce cost and weight by decreasing the number of lenses. The group 1A having positive power functions as a condenser lens for condensing the beam (diverging beam) emitted from the emitting end 21. While cemented lenses in the group 1C and/or the second group (especially, their cementing surfaces) mainly have the function of correcting the axial chromatic aberration, they can not correct chromatic aberration of magnification. The condition (4a) is for giving the group 1A proper chromatic aberration and thereby correcting the axial chromatic aberration and the chromatic aberration of magnification in total. In the case where the group 1A is composed of a single lens, the chromatic aberration of magnification can be suppressed effectively by use of a single lens having an Abbe number $\nu 1$ satisfying the condition (4a). For providing the single lens (group 1A) with the axial chromatic aberration correction function, an Abbe number $\nu 1A$ satisfying the following condition (4a) is given to the single lens:

$$\nu 1A < 30 \tag{4a}$$

The condensing optical system 10a is composed to satisfy the following conditions (2a) and (3a):

$$0.1 < d0/f1A < 0.5 \tag{2a}$$

$$0.2 < |f1A/f1| < 0.8 \tag{3a}$$

where "d0" denotes the distance from the emitting end 21 to the first surface r1 of the condensing optical system 10a, "f1" denotes the composite focal length of the first group G1, and "f1A" denotes the focal length of the group 1A.

The point source of light constantly moves for scanning the beam. Meanwhile, the beam emitted from the point source originally diverges, that is, spreads (diverges) wider as the distance from the point source becomes longer. In the condensing optical system, the beam diverging is condensed by the group 1A which is placed just after the point source. Therefore, the diameter of the lens of the group 1A can be reduced and the whole condensing optical system can be miniaturized further as the group 1A is placed nearer to the point source. However, placing the group 1A too close to the point source might cause contact of the lens of the group 1A with the point source which is moving. The condition (2a) specifies such a positional relationship between the point source of light and the group 1A and the miniaturization of the condensing optical system. The miniaturization becomes difficult when the value d0/f1A exceeds the upper limit of the condition (2a), while the group 1A makes contact with the point source when the value falls below the lower limit.

As mentioned above, the group 1A has positive power for condensing the diverging beam emitted from the point source. The condition (3a) is for properly setting the power of the group 1A, considering power balance with the power of the whole system. When the value |f1A/f1| falls below the lower limit of the condition (3a), the power of the group 1A becomes too strong, by which distortion might be caused. When the value exceeds the upper limit, the power of the group 1A becomes too weak, causing an exceedingly large diameter of the lens forming the group 1A.

The conditions (2a) and (3a) are those for miniaturizing the condensing optical system 10a. By satisfying both the conditions (2a) and (3a), the condensing optical system 10a is allowed to suppress various aberrations (distortion, etc.) satisfactorily while being miniaturized.

A concave surface r4 of the group 1A facing toward the cover glass 80 is formed in order to correct field curvature. Incidentally, the beam emerging from the group 1B diverges due to the concave surface r4. The group 1C is provided with positive power in order to reduce the divergence of the beam. A cementing surface r6 of the group 1C has a function of correcting the axial chromatic aberration.

The group G1 includes a cemented lens (composed of a biconcave lens and a biconvex lens) and at least one positive single lens. The cemented lens has negative power as a whole. A strongly diverging surface r16 of the cemented lens facing toward the emitting end 21 of the optical fiber 20 has a function of correcting spherical aberration and coma. A cementing surface r17 of the cemented lens contributes to correction of the axial chromatic aberration in cooperation with the aforementioned surface r6. As above, the axial chromatic aberration correcting function is given to both the first group G1 and the second group G2 in this embodiment, by which the axial chromatic aberration is corrected in each group G1, G2.

As described above, the second group G2 held by the lens driver 90 to be slidable is in a state suppressing various aberrations by itself, by the employment of the cemented lens. Incidentally, the positive power is distributed to three single lenses in the second group G2 in this embodiment, by which spherical aberration and coma generated in each lens are reduced to low levels. The two single lenses of the second group G2 on the cover glass side and the cemented lens are set exactly in a retrofocus configuration, by which a sufficient working distance is secured.

In the condensing optical system 10a described above, it is necessary to prevent variation of magnification or an increase in aberration which might be caused by the movement of the second group G2.

First, in order to avoid the increase in aberration which can be caused by the movement of the second group G2, the condensing optical system 10a is configured so that the beam emerging from the deflecting group GD and incident upon the second group G2 will be substantially a parallel beam. Further, decentering tends to occur due to individual differences (e.g. processing error) of the deflecting group (specifically, a beam traveling on the optical axis of the first group while traveling off the optical axis of the second group due to individual differences of the deflecting group). Further, for reducing the effect of decentering of the deflecting group GD, the deflecting group GD is made of optical members that are formed of planes only. However, in the case where the deflecting group GD is made of optical members formed of planes only, the aforementioned parallelism of the beam incident upon the second group G2 further requires parallelism of the beam emerging from the first group G1 and incident upon the deflecting group GD. Therefore, the first group G1 and the second group G2 in the condensing optical system 10a are configured to satisfy the following condition (5a):

$$0.97 < f2 \times m/f1 < 1.03 \quad (5a)$$

where "f1" denotes the composite focal length of the first group G1, "f2" denotes the composite focal length of the second group G2, and "m" denotes magnification of the condensing optical system 10a.

By configuring the groups G1 and G2 to satisfy the condition (5a), that is, to let the beam emerging from the deflecting group GD and incident upon the second group G2 be substantially a parallel beam, relative positioning of the first group G1 and the second group G2 in the confocal optical system 100a becomes easy and thereby the need of keeping high assembly accuracy can be eliminated.

If the interval (length in air (hereinafter referred to as "in-air length")) occupied by the deflecting group gets long, vignetting might be caused by the incidence of off-axis beams (having certain angles relative to the optical axis) into the second group. The deflecting group GD in this embodiment is implemented by a prism since the in-air length can be reduced compared to a deflecting group implemented by mirrors. The prism is placed so that the incident beam will be totally reflected by at least one optical surface of the prism. By use of the total reflection, loss of light quantity during the deflection by the deflecting group GD is reduced and thereby usage efficiency of light can be increased. The type of the prism employed for the deflecting group GD varies depending on the deflecting angle (how many degrees the optical path of the beam should be deflected) necessary for laterally viewing the living tissue 400, that is, depending on the angle θ between the optical axis of the first group G1 and that of the second group G2. Specifically, the deflecting group GD can be implemented by a two-reflection prism when the angle θ is 60° or less (see first and third examples described below).

For example, a triangular prism is preferably used when an angle θ between the optical axis of the first group and that of the second group is over 60°. A rectangular prism can be used when the angle θ is 90°. In the case of a rectangular prism, a short in-air length can be attained by designing the hypotenuse face of the rectangular prism as a total reflection surface. When the angle θ is 60° or less, a prism deflecting the beam by reflecting it twice (e.g. a prism having a pentagonal cross section containing the optical axis, hereinafter referred to as a "two-reflection prism") is suitable for reducing the in-air length. Each of the above prisms may either be a single prism shaped as above or a cemented prism made of two or more polygonal prisms. When it is difficult to design and place a two-reflection prism to let both of the two reflecting surfaces totally reflect the beam, one of the reflecting surfaces may be coated with metal, etc.

In the condensing optical system 10a of the second embodiment, the angle θ is set within the following condition (6a) so that the incident beam will satisfy the total reflection condition in the deflecting group GD.

$$35°<θ<105° \quad (6a)$$

When the angle θ falls below the lower limit of the condition (6a), vignetting might be caused by off-axis beams that do not satisfy the total reflection condition of a two-reflection prism. Meanwhile, when the angle θ exceeds the upper limit, vignetting might be caused by off-axis beams that do not satisfy the total reflection condition of a triangular prism.

Further, the condensing optical system 10a is configured to satisfy the following condition (1a):

$$0.1<|m \times NA|<0.2 \quad (1a)$$

where "m" denotes the magnification and "NA" denotes a numerical aperture on the subject surface side of the condensing optical system 10a. The condensing optical system 10a satisfying the condition (1a) is capable of emitting the beam (emerging from the emitting end 21) from the tip of the flexible tube and condensing the beam on the subject surface while minimizing the loss of light quantity and suppressing aberrations.

In confocal optical systems of the so-called fiber scan type (using the emitting end of a single-mode optical fiber both as the point source of light and as the pinhole for confocal observation), the optical axis of the condensing optical system is required to be substantially in line with the optical fiber (placed in the lengthwise direction of the flexible tube). Therefore, the condensing optical system described above is especially suitable when the confocal optical system is employed for an integrated endoscope of a lateral view type. In this case, the condensing optical system can be accommodated in the flexible tube without the need of upsizing the flexible tube by placing the condensing optical system so that the optical axis of the first group will be substantially in line with the optical fiber.

In the following, three concrete examples of the condensing optical system 10a in accordance to the second embodiment of the present invention will be described in detail.

EXAMPLE 2-1

FIG. 12 is a schematic diagram showing lens arrangement of a condensing optical system 10a as a first example of the second embodiment. The following Table 7 shows specific numerical configuration of the condensing optical system 10a of the first example.

TABLE 7

| No. | r | d | n | ν | REMARKS |
|---|---|---|---|---|---|
| 0 |  | 0.900 |  |  | EMITTING END 21 |
| 1 | 5.242 | 1.064 | 1.92286 | 18.9 | G1 (1A) |
| 2 | −4.231 | 0.128 |  |  |  |
| 3 | 1.812 | 0.795 | 1.51633 | 64.1 | G1 (1B) |
| 4 | 1.228 | 1.269 |  |  |  |

TABLE 7-continued

| No. | r | d | n | ν | REMARKS |
|---|---|---|---|---|---|
| 5 | −0.991 | 0.577 | 1.84666 | 23.8 | G1 (1C) |
| 6 | 244.027 | 1.218 | 1.77250 | 49.6 |  |
| 7 | −2.035 | 0.128 |  |  |  |
| 8 | −73.520 | 0.833 | 1.77250 | 49.6 |  |
| 9 | −5.049 | 0.256 |  |  |  |
| 10 | ∞ | 3.165 | 1.88300 | 40.8 | GD |
| 11 | ∞ | 0.010 |  |  |  |
| 12 | ∞ | 0.500 | 1.88300 | 40.8 |  |
| 13 | ∞ | 0.200 |  |  |  |
| 14 | 4.564 | 0.744 | 1.88300 | 40.8 | G2 |
| 15 | 13.138 | 0.397 |  |  |  |
| 16 | −3.900 | 0.513 | 1.84666 | 23.8 |  |
| 17 | 2.914 | 1.282 | 1.74400 | 44.8 |  |
| 18 | −7.963 | 0.885 |  |  |  |
| 19 | 7.987 | 0.756 | 1.88300 | 40.8 |  |
| 20 | −7.987 | 0.128 |  |  |  |
| 21 | 2.350 | 1.231 | 1.88300 | 40.8 |  |
| 22 | 3.095 | 1.030 |  |  |  |
| 23 | ∞ | 0.385 | 1.51633 | 64.1 | COVER GLASS 80 |
| 24 | ∞ | — |  |  |  |

Similarly to the tables in the first embodiment, "No." in Table 7 denotes the surface number, "r" denotes the curvature radius [mm] of each lens surface, "d" denotes the lens thickness or lens interval [mm], "n" denotes the refractive index at the D line wavelength (588 nm), "ν" denotes the Abbe number at the D line wavelength, and "REMARKS" denotes the optical element indicated by each surface number (ditto for following tables).

In the condensing optical system 10a of the first the second embodiment, the angle θ between the optical axis of the first group G1 and that of the second group G2 is set to 60°. Therefore, two prisms are employed for the deflecting group GD and the optical path of the beam is deflected by letting the prisms reflect the beam twice.

EXAMPLE 2-2

Figure 13:
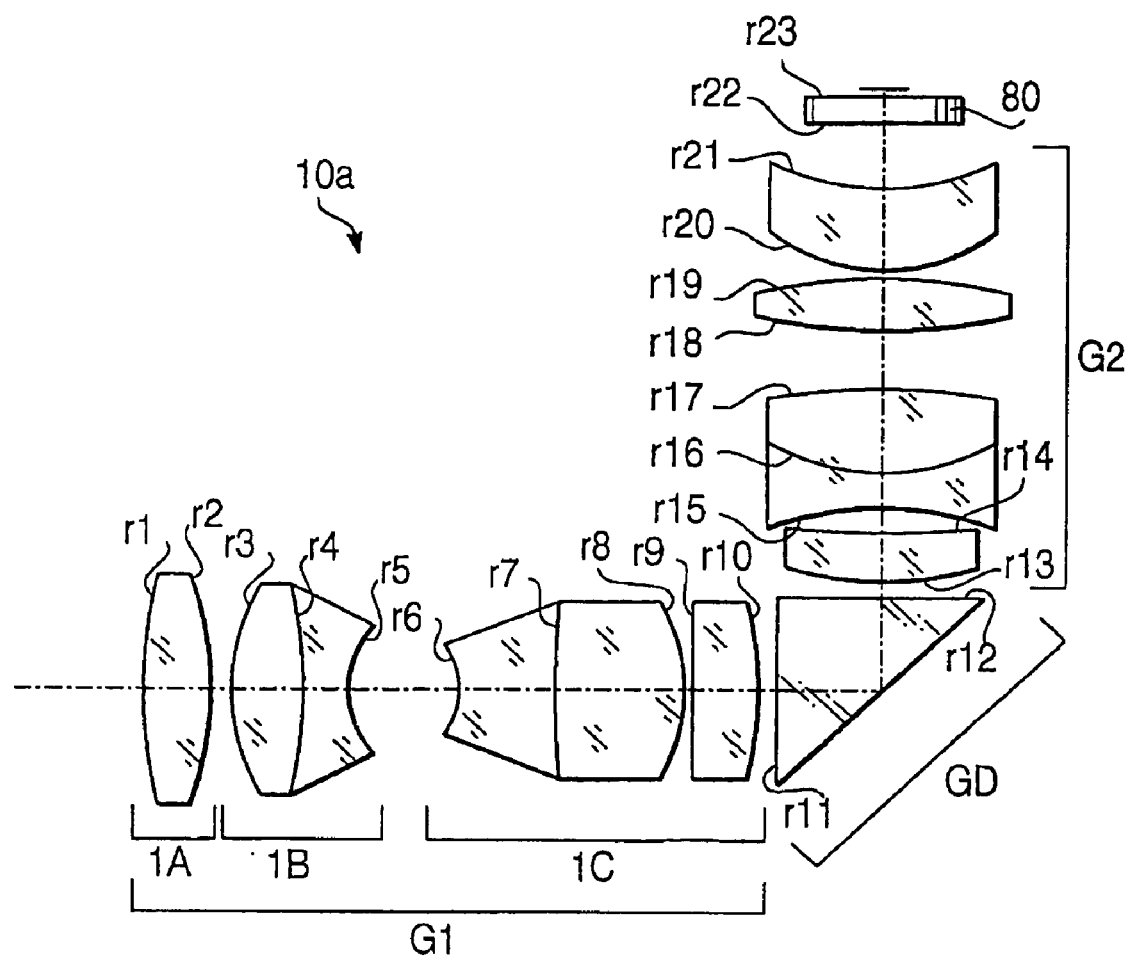
FIG. 13 is a schematic diagram showing lens arrangement of a condensing optical system as a second example of the second embodiment.

FIG. 13 is a schematic diagram showing lens arrangement of a condensing optical system 10a as a second example of the second embodiment. The following Table 8 shows specific numerical configuration of the condensing optical system 10a of the second example.

TABLE 8

| No. | r | d | n | ν | REMARKS |
|---|---|---|---|---|---|
| 0 |  | 0.566 |  |  | EMITTING END 21 |
| 1 | 6.768 | 0.697 | 1.92286 | 18.9 | G1 (1A) |
| 2 | −4.414 | 0.210 |  |  |  |
| 3 | 2.554 | 0.758 | 1.84666 | 23.8 | G1 (1B) |
| 4 | −6.519 | 0.458 | 1.51633 | 64.1 |  |
| 5 | 1.117 | 1.236 |  |  |  |
| 6 | −0.876 | 1.047 | 1.84666 | 23.8 | G1 (1C) |
| 7 | 11.986 | 1.398 | 1.77250 | 49.6 |  |
| 8 | −2.407 | 0.100 |  |  |  |
| 9 | −24.305 | 0.701 | 1.77250 | 49.6 |  |
| 10 | −4.439 | 0.200 |  |  |  |
| 11 | ∞ | 2.200 | 1.88300 | 40.8 | GD |
| 12 | ∞ | 0.200 |  |  |  |
| 13 | 3.560 | 0.576 | 1.88300 | 40.8 | G2 |
| 14 | 10.241 | 0.306 |  |  |  |
| 15 | −3.042 | 0.400 | 1.84666 | 23.8 |  |
| 16 | 2.273 | 1.009 | 1.74400 | 44.8 |  |
| 17 | −6.211 | 0.689 |  |  |  |
| 18 | 6.231 | 0.586 | 1.88300 | 40.8 |  |
| 19 | −6.231 | 0.100 |  |  |  |
| 20 | 1.833 | 0.956 | 1.88300 | 40.8 |  |

TABLE 8-continued

| No. | r | d | n | v | REMARKS |
|---|---|---|---|---|---|
| 21 | 2.414 | 0.783 | | | |
| 22 | ∞ | 0.300 | 1.51633 | 64.1 | COVER |
| 23 | ∞ | — | | | GLASS 80 |

In the condensing optical system 10a of the second example of the second embodiment, the angle θ is set to 90°. Therefore, a rectangular prism is employed for the deflecting group GD and the optical path is deflected by letting the hypotenuse face of the rectangular prism totally reflect the incident beam.

EXAMPLE 2-3

Figure 14:
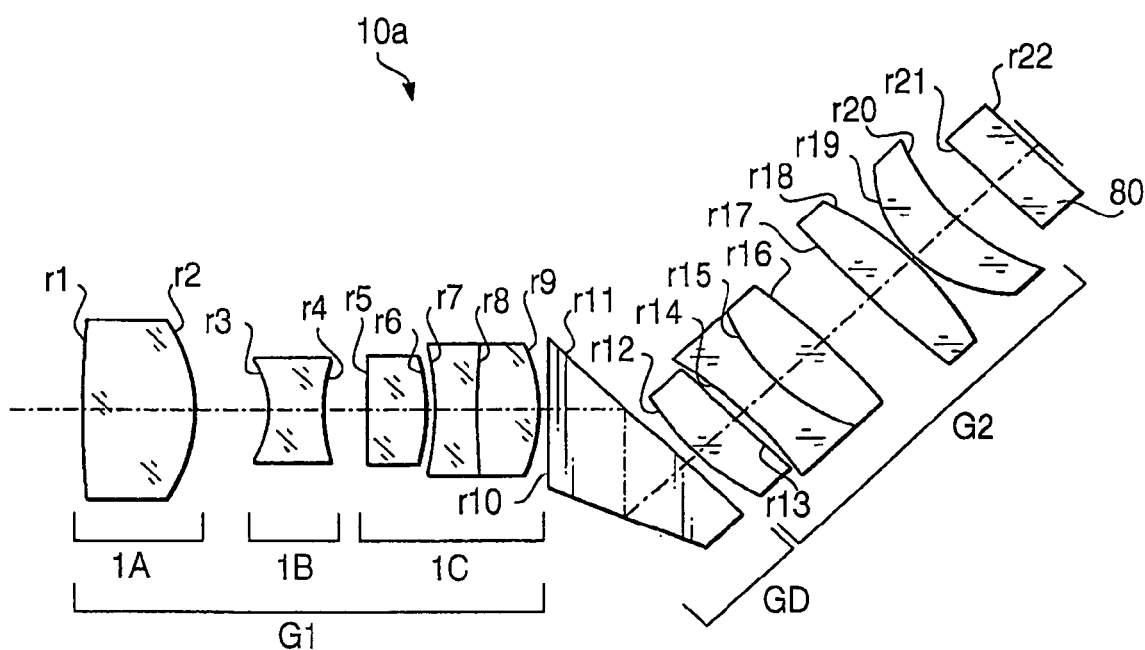
FIG. 14 is a schematic diagram showing lens arrangement of a condensing optical system as a third example of the second embodiment.

FIG. 14 is a schematic diagram showing lens arrangement of a condensing optical system 10a as a third example of the second embodiment. The following Table 9 shows specific numerical configuration of the condensing optical system 10a of the third example.

TABLE 9

| No. | r | d | n | v | REMARKS |
|---|---|---|---|---|---|
| 0 | | 0.566 | | | EMITTING END 21 |
| 1 | 20.605 | 1.388 | 1.84666 | 23.8 | G1 (1A) |
| 2 | −2.371 | 0.932 | | | |
| 3 | −1.377 | 0.652 | 1.51633 | 64.1 | G1 (1B) |
| 4 | 2.251 | 0.539 | | | |
| 5 | 65.406 | 0.733 | 1.77250 | 49.6 | G1 (1C) |
| 6 | −3.343 | 0.109 | | | |
| 7 | −5.097 | 0.543 | 1.84666 | 23.8 | |
| 8 | 8.772 | 0.790 | 1.72000 | 50.2 | |
| 9 | −2.449 | 0.130 | | | |
| 10 | ∞ | 3.500 | 1.88300 | 40.8 | GD |
| 11 | ∞ | 0.200 | | | |
| 12 | 3.402 | 0.687 | 1.74950 | 35.3 | G2 |
| 13 | 248.843 | 0.143 | | | |
| 14 | −4.131 | 0.572 | 1.84666 | 23.8 | |
| 15 | 2.789 | 0.800 | 1.62230 | 53.2 | |
| 16 | −9.924 | 0.837 | | | |
| 17 | 11.211 | 0.722 | 1.77250 | 49.6 | |
| 18 | −4.263 | 0.046 | | | |
| 19 | 1.737 | 0.744 | 1.88300 | 40.8 | |
| 20 | 2.696 | 0.662 | | | |
| 21 | ∞ | 0.687 | 1.51633 | 64.1 | COVER |
| 22 | ∞ | — | | | GLASS 80 |

In the condensing optical system 10a of the third example of the second embodiment, the angle θ is set to 45°. Therefore, a two-reflection prism is employed for the deflecting group GD.

As shown in FIGS. 12 through 14, in the first through third examples of the second embodiment, the group 1A is composed of a single lens only in order to reduce the weight of the condensing optical system 10a by decreasing the number of lenses. While the group 1B is composed of one single lens in the first and third examples, the second example employs a cemented lens and thereby copes with a high NA of approximately 0.5. In each example, the second group G2 includes three single lenses and positive power is distributed to the three single lenses as mentioned above, by which spherical aberration and coma, occurring when a spherical lens is used for the second group G2, are suppressed well.

The following Table 10 shows the values included in the expressions of the aforementioned conditions (1)-(7) regarding the condensing optical systems 10a of the first through third examples of the second embodiment. In Table 10, "H1" denotes the distance from the first surface r1 to the front principal point H. The values of the expressions of the conditions (1)-(7) obtained by substituting the values of Table into the expressions will be shown in Table 11.

TABLE 10

| | EX. 1 | EX. 2 | EX. 3 |
|---|---|---|---|
| m | −0.438 | −0.265 | −0.422 |
| NA | 0.30 | 0.50 | 0.40 |
| f | −2.803 | −1.478 | −25.286 |
| f1 | 5.889 | 7.583 | 5.07 |
| f2 | 2.589 | 2.017 | 2.141 |
| f1A | 2.682 | 2.984 | 2.583 |
| d0 | 0.900 | 0.566 | 0.545 |
| v1A | 18.9 | 18.9 | 23.9 |
| θ | 60 | 90 | 45 |
| s | 3.205 | 2.546 | 68.86 |
| H1 | −10.105 | −7.612 | −85.705 |

TABLE 11

| CONDITION | EX. 1 | EX. 2 | EX. 3 |
|---|---|---|---|
| (1) | 0.131 | 0.133 | 0.169 |
| (2) | 0.336 | 0.190 | 0.211 |
| (3) | 0.455 | 0.394 | 0.509 |
| (4) | 18.9 | 18.9 | 23.9 |
| (5) | 0.996 | 0.996 | 0.999 |
| (6) | 60 | 90 | 45 |
| (7) | 0.875 | 0.581 | 0.367 |

Figures 15A, 15B, 15C, 15D:
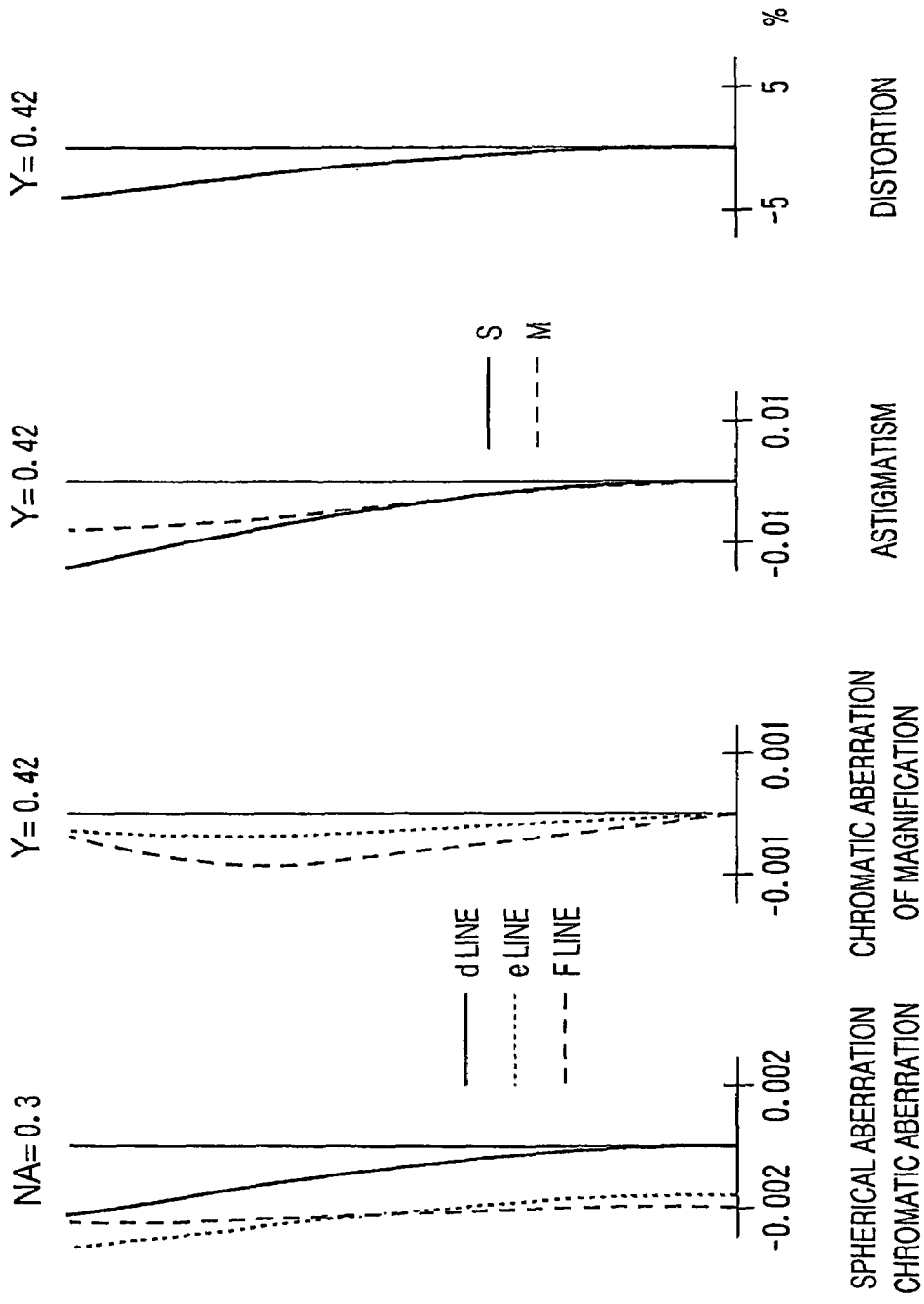
FIGS. 15A through 15D are graphs showing aberrations occurring in the condensing optical system of the first example of the second embodiment.
Figures 17A, 17B, 17C, 17D:
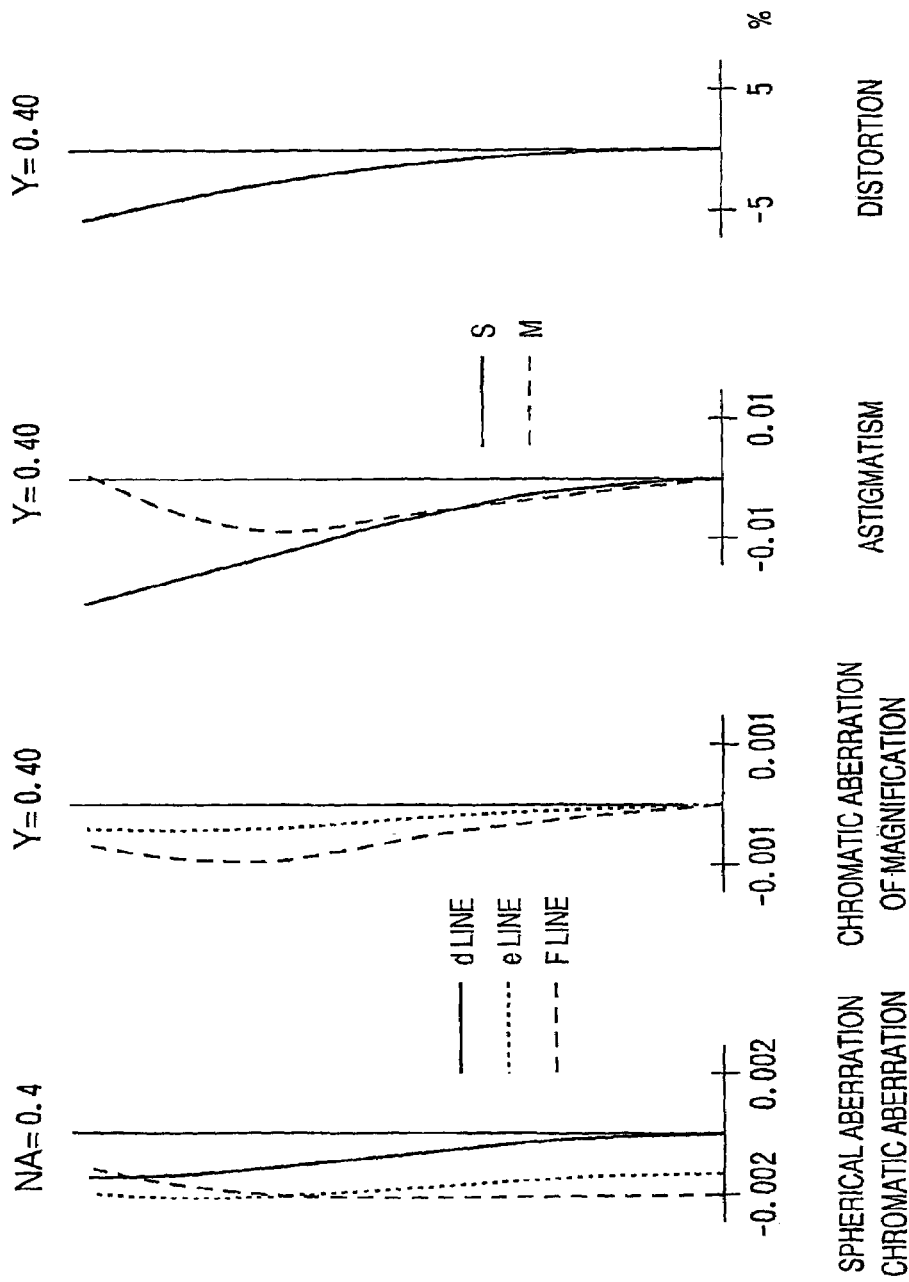
FIGS. 17A through 17D are graphs showing aberrations occurring in the condensing optical system of the third example of the second embodiment.

FIGS. 15A through 17D are graphs showing aberrations occurring in the condensing optical systems 10a of the first through third examples of the second embodiment, in which FIGS. 15A, 16A and 17A show spherical aberration and axial chromatic aberration, FIGS. 15B, 16B and 17B show chromatic aberration of magnification, FIGS. 15C, 16C and 17C show astigmatism, and FIGS. 15D, 16D and 17D show distortion. In the graphs 15A, 16A and 17A showing spherical aberration and axial chromatic aberration, "E line" denotes a wavelength 546 nm and "F line" denotes a wavelength 486 nm. In the graphs 15C, 16C and 17C showing astigmatism, "S" denotes sagittal and "M" denotes meridional. Each of the first through third examples satisfies all the conditions (1)-(7) as shown in Table 11. Therefore, the aberrations are all suppressed excellently in the condensing optical systems 10a of the first through third examples of the second embodiment.

As described above, by the second embodiment in accordance with the present invention, a condensing optical system suitable for a lateral view confocal optical system (implementing the three-dimensional scanning by swinging the point source of light) and capable of satisfactorily suppressing various aberrations and reducing loss of light quantity is obtained. The confocal optical system equipped with such a condensing optical system is capable of securing a wide scan range without the need of upsizing even though it is of a lateral view type. By use of such a confocal optical system, a lateral view integrated endoscope with a flexible tube almost as thin as that of a direct view integrated endoscope can be realized.

While the present invention has been described with reference to the particular illustrative embodiments, it is not to be restricted by those embodiments but only by the appended claims. It is to be appreciated that those skilled in the art can change or modify the embodiments without departing from the scope and spirit of the present invention.

The present disclosure relates to the subject matter contained in Japanese Patent Applications No. 2003-314204, filed on Sep. 5, 2003, and No. 2003-357896, filed on Oct. 17, 2003, which are expressly incorporated herein by reference in their entireties.

What is claimed is:

1. A condensing optical system installed in a scanning confocal optical system for obtaining images of a subject surface by scanning a beam emitted from a point source of light by moving the point source which serves as a pinhole for confocal observation,
wherein the condensing optical system is configured to satisfy the following condition (1):

$$0.1 < |m \times NA| < 0.2 \quad (1)$$

where "m" denotes magnification of the condensing optical system and "NA" denotes a numerical aperture of the condensing optical system on its subject surface side.

2. The condensing optical system according to claim 1, comprising the following three groups from its point source side:
a first group having positive power;
a second group including at least a lens with a concave surface facing toward the subject surface; and
a third group having positive power.

3. The condensing optical system according to claim 2, wherein the condensing optical system is configured to satisfy the following conditions (2) and (3):

$$0.1 < d0/f1 < 0.5 \quad (2)$$

$$0.2 < |f1/f| < 2.0 \quad (3)$$

where "d0" denotes a distance from the point source of light to a first surface of the condensing optical system, "f" denotes a composite focal length of the whole condensing optical system, and "f1" denotes a focal length of the first group.

4. The condensing optical system according to claim 2, wherein the first group is composed of a single lens having an Abbe number ν1 satisfying the following condition (4):

$$\nu 1 < 30 \quad (4)$$

5. The condensing optical system according to claim 2, wherein the third group includes the following three groups from its point source side:
a group 3A including at least one positive single lens and a cemented lens made of a positive lens and a negative lens, having positive power as a whole;
a group 3B including a cemented lens made of a biconcave lens and a biconvex lens, having negative power as a whole; and
a group 3C including at least one positive single lens, having positive power as a whole.

6. The condensing optical system according to claim 5, wherein the group 3A includes two single lenses having positive power.

7. The condensing optical system according to claim 5, wherein the group 3C includes a biconvex lens and a positive meniscus lens.

8. The condensing optical system according to claim 2, wherein the second group includes a single lens or a cemented lens.

9. The condensing optical system according to claim 1, comprising the following elements from its point source side:
a first group having positive power;
a deflecting group including at least one deflecting member;
a second group having positive power; and
a cover glass,
wherein a condensing position of the beam condensed by the condensing optical system is moved in an optical axis direction of the condensing optical system at least by changing a distance between the second group and the cover glass.

10. The condensing optical system according to claim 9, wherein the first group includes the following three groups from its point source side:
a group 1A having positive power;
a group 1B including either a single lens or cemented lens with at least a concave surface facing toward the cover glass; and
a group 1C having positive power including a cemented lens and a single lens.

11. The condensing optical system according to claim 10, wherein the condensing optical system is configured to satisfy the following conditions (2a) and (3a):

$$0.1 < d0/f1A < 0.5 \quad (2a)$$

$$0.2 < |f1A/f1| < 0.8 \quad (3a)$$

where "d0" denotes a distance from the point source of light to a first surface of the condensing optical system, "f1" denotes a composite focal length of the first group, and "f1A" denotes a focal length of the group 1A.

12. The condensing optical system according to claim 10, wherein the group 1A is composed of a single lens having an Abbe number ν1A satisfying the following condition (4a):

$$\nu 1A < 30 \quad (4a)$$

13. The condensing optical system according to claim 9, wherein the second group includes at least one positive single lens and a cemented lens made of a positive lens and a negative lens.

14. The condensing optical system according to claim 13, wherein the second group includes three positive single lenses.

15. The condensing optical system according to claim 9, wherein the beam emerging from the deflecting group and incident upon the second group is substantially a parallel beam.

16. The condensing optical system according to claim 15, wherein the first group and the second group are configured to satisfy the following condition (5a):

$$0.97 < f2 \times m/f1 < 1.03 \quad (5a)$$

where "f1" denotes a composite focal length of the first group, "f2" denotes a composite focal length of the second group, and "m" denotes magnification of the condensing optical system.

17. The condensing optical system according to claim 16, wherein the deflecting group is formed of optical members that are made of planes only.

18. The condensing optical system according to claim 9, wherein:
the deflecting group includes a prism which is placed so that the incident beam will be totally reflected by at least one optical surface of the prism, and
an angle θ between an optical axis of the first group and that of the second group is set to satisfy the following condition (6a):

$$35° < \theta < 105° \quad (6a)$$

19. The condensing optical system according to claim 9, wherein the first group, the deflecting group and the cover glass are fixed inside the scanning confocal optical system.

20. A condensing optical system installed in a scanning confocal optical system for obtaining images of a subject surface by scanning a beam emitted from a point source of light by moving the point source which serves as a pinhole for confocal observation, comprising the following elements from its point source side:
   a first group having positive power;
   a deflecting group including at least one deflecting member;
   a second group having positive power; and
   a cover glass,
wherein a condensing position of the beam condensed by the condensing optical system is moved in an optical axis direction of the condensing optical system at least by changing a distance between the second group and the cover glass.

21. A confocal optical system comprising:
   a point source of light serving as a pinhole for confocal observation;
   a condensing optical system for condensing a beam emitted from the point source, being configured to satisfy the following condition (1):

$$0.1 < |m \times NA| < 0.2 \tag{1}$$

where "m" denotes magnification of the condensing optical system and "NA" denotes a numerical aperture of the condensing optical system on its subject surface side;
   a cover glass provided between the condensing optical system and a condensing position of the beam condensed by the condensing optical system;
   a scanning unit for scanning the beam by moving the point source of light at least on a surface substantially orthogonal to an optical axis of the condensing optical system; and
   a condensing position moving unit for moving the condensing position in an optical axis direction of the condensing optical system by changing a distance between the condensing optical system and the cover glass.

22. The confocal optical system according to claim 21, wherein:
   the surface substantially orthogonal to the optical axis of the condensing optical system is a curved surface having its center of curvature on the optical axis of the condensing optical system, and
   the confocal optical system is configured to satisfy the following condition (5):

$$0.1 < -f/s < 1.0 \tag{5}$$

where "f" denotes a composite focal length of the whole condensing optical system and "s" denotes a distance from a front principal point of the condensing optical system to an intersection point of the optical axis of the condensing optical system and an elongation of a principal ray of the beam emitted from the moving point source regarding a direction toward the subject surface as positive.

23. The confocal optical system according to claim 22, wherein:
   the point source of light is an emitting end of an optical fiber which is provided between a light emitting unit and the condensing optical system to be substantially coaxial with the optical axis of the condensing optical system, and
   the scanning unit moves the point source of light on the curved surface by bending a part of the optical fiber in the vicinity of the emitting end.

24. A confocal optical system comprising:
   a point source of light serving as a pinhole for confocal observation;
   a condensing optical system for condensing a beam emitted from the point source, including a first group having positive power, a deflecting group including at least one deflecting member, a second group having positive power, and a cover glass from its point source side;
   a scanning unit for scanning the beam by moving the point source of light at least on a surface substantially orthogonal to an optical axis of the condensing optical system; and
   a condensing position moving unit for moving a condensing position of the beam condensed by the condensing optical system in an optical axis direction of the condensing optical system at least by changing a distance between the second group and the cover glass.

25. The confocal optical system according to claim 24, wherein:
   the surface substantially orthogonal to the optical axis of the condensing optical system is a curved surface having its center of curvature on the optical axis of the condensing optical system, and
   the confocal optical system is configured to satisfy the following condition (7a):

$$0.1 < -f/s < 1.0 \tag{7a}$$

where "f" denotes a composite focal length of the whole condensing optical system and "s" denotes a distance from a front principal point of the condensing optical system to an intersection point of the optical axis of the condensing optical system and an elongation of a principal ray of the beam emitted from the moving point source regarding a direction toward the subject surface as positive.

26. The confocal optical system according to claim 25, wherein:
   the point source of light is an emitting end of an optical fiber which is provided between a light emitting unit and the condensing optical system to be substantially coaxial with the optical axis of the condensing optical system, and
   the scanning unit moves the point source of light on the curved surface by bending a part of the optical fiber in the vicinity of the emitting end.

27. A scanning confocal endoscope, comprising a confocal optical system including:
   a point source of light serving as a pinhole for confocal observation;
   a condensing optical system for condensing a beam emitted from the point source, being configured to satisfy the following condition (1):

$$0.1 < |m \times NA| < 0.2 \tag{1}$$

where "m" denotes magnification of the condensing optical system and "NA" denotes a numerical aperture of the condensing optical system on its subject surface side;
   a cover glass provided between the condensing optical system and a condensing position of the beam condensed by the condensing optical system;
   a scanning unit for scanning the beam by moving the point source of light at least on a surface substantially orthogonal to an optical axis of the condensing optical system; and a condensing position moving unit for moving the condensing position in an optical axis direction of the condensing optical system by changing a distance between the condensing optical system and the cover glass.

28. A scanning confocal endoscope, comprising a confocal optical system including:

a point source of light serving as a pinhole for confocal-observation;

a condensing optical system for condensing a beam emitted from the point source, including a first group having positive power, a deflecting group including at least one deflecting member, a second group having positive power, and a cover glass from its point source side;

a scanning unit for scanning the beam by moving the point source of light at least on a surface substantially orthogonal to an optical axis of the condensing optical system; and a condensing position moving unit for moving a condensing position of the beam condensed by the condensing optical system in an optical axis direction of the condensing optical system at least by changing a distance between the second group and the cover glass.

* * * * *